US010226066B2

(12) United States Patent
Moldoveanu et al.

(10) Patent No.: US 10,226,066 B2
(45) Date of Patent: Mar. 12, 2019

(54) ROSEMARY IN A TOBACCO BLEND

(71) Applicant: R.J. REYNOLDS TOBACCO COMPANY, Winston-Salem, NC (US)

(72) Inventors: Serban C. Moldoveanu, Winston-Salem, NC (US); Wayne Allen Scott, Lewisville, NC (US)

(73) Assignee: R.J. REYNOLDS TOBACCO COMPANY, Winston-Salem, NC (US)

(*) Notice: Subject to any disclaimer, the term of this patent is extended or adjusted under 35 U.S.C. 154(b) by 199 days.

(21) Appl. No.: 15/062,907

(22) Filed: Mar. 7, 2016

(65) Prior Publication Data

US 2017/0251715 A1 Sep. 7, 2017

(51) Int. Cl.
*A24B 15/30* (2006.01)
*A61K 9/00* (2006.01)
*A61K 31/56* (2006.01)
*A61K 36/53* (2006.01)
*A24B 13/00* (2006.01)
*A24B 15/34* (2006.01)
*A61K 36/81* (2006.01)

(52) U.S. Cl.
CPC ............ *A24B 15/302* (2013.01); *A24B 13/00* (2013.01); *A24B 15/345* (2013.01); *A61K 9/007* (2013.01); *A61K 31/56* (2013.01); *A61K 36/53* (2013.01); *A61K 36/81* (2013.01)

(58) Field of Classification Search
CPC ....... A24B 15/302; A24B 13/00; A24B 15/16; A24B 15/10; A24B 15/18; A24B 15/183; A24B 15/22; A24B 15/241; A24B 15/246
See application file for complete search history.

(56) References Cited

U.S. PATENT DOCUMENTS

| | | |
|---|---|---|
| 4,508,525 A | 4/1985 | Berger |
| 4,836,224 A | 6/1989 | Lawson et al. |
| 4,920,990 A | 5/1990 | Lawrence |
| 4,924,883 A | 5/1990 | Perfetti |
| 4,924,888 A | 5/1990 | Perfetti |
| 4,991,596 A | 2/1991 | Lawrence et al. |
| 5,056,537 A | 10/1991 | Brown |
| 5,101,839 A | 4/1992 | Jakob |
| 5,105,834 A | 4/1992 | Saintsing |
| 5,105,838 A | 4/1992 | White |
| 5,159,942 A | 11/1992 | Brinkley |
| 5,220,930 A | 6/1993 | Gentry |
| 5,360,023 A | 11/1994 | Blakley |
| 5,859,293 A * | 1/1999 | Bailey .................... A23L 3/3472 562/466 |
| 6,701,936 B2 | 3/2004 | Shafer |
| 6,730,832 B1 | 5/2004 | Dominguez |
| 6,827,951 B2 | 12/2004 | Newmark et al. |
| 6,982,099 B2 | 1/2006 | Newmark et al. |
| 7,325,548 B2 * | 2/2008 | Enslin .................... A24B 15/28 131/347 |
| 7,900,639 B2 | 3/2011 | Perfetti |
| 8,434,496 B2 | 5/2013 | Chen et al. |
| 8,567,412 B2 | 10/2013 | Emami |
| 8,991,403 B2 | 3/2015 | Chen et al. |
| 8,994,072 B2 | 3/2015 | Kerber et al. |
| 9,149,071 B2 | 10/2015 | Kizer et al. |
| 9,155,321 B2 | 10/2015 | Cantrell et al. |
| 9,155,334 B2 | 10/2015 | Moldoveanu et al. |
| 9,637,706 B2 * | 5/2017 | Indrasena ............. C11B 5/0092 |
| 2003/0075193 A1 | 4/2003 | Li |
| 2003/0131859 A1 | 7/2003 | Li |
| 2004/0084056 A1 | 5/2004 | Lawson |
| 2004/0237984 A1 | 12/2004 | Figlar |
| 2004/0255965 A1 | 12/2004 | Perfetti |
| 2005/0066982 A1 | 3/2005 | Clark |
| 2005/0066984 A1 | 3/2005 | Crooks |
| 2005/0066986 A1 | 3/2005 | Nestor |
| 2005/0268925 A1 | 12/2005 | Schluter |
| 2006/0130861 A1 | 6/2006 | Luan |
| 2006/0174899 A9 | 8/2006 | Luan |
| 2010/0300463 A1 * | 12/2010 | Chen .................... A24B 15/302 131/274 |
| 2011/0155157 A1 | 6/2011 | Emami |
| 2012/0234334 A1 * | 9/2012 | Chen ........................ A24B 3/00 131/305 |
| 2013/0217768 A1 * | 8/2013 | Nahas .................... A61K 36/53 514/533 |
| 2015/0068544 A1 | 3/2015 | Moldoveanu et al. |
| 2015/0068545 A1 | 3/2015 | Moldoveanu et al. |
| 2015/0101627 A1 | 4/2015 | Marshall et al. |

FOREIGN PATENT DOCUMENTS

| | | |
|---|---|---|
| EP | 0 970 625 | 1/2000 |
| EP | 2 606 751 | 6/2013 |
| WO | WO-2002/037990 | 5/2002 |

OTHER PUBLICATIONS

Basile, Annamaria, Maria M. Jimenez-Carmona, and Anthony A. Clifford, "Extraction of Rosemary by Superheated Water", Published Dec. 1, 1998, Journal of Agricultural Food Chemistry, vol. 46, No. 12, pp. 5205-5209.*
Rao et al., "Rosemary (*Rosmarinus Officinalis* L.): Impact of Drying on its Flavor Quality", 1998, Journal of Food Quality, vol. 21, p. 107-115. (Year: 1998).*
Moldoveanu, "The Utilization of Gas Chromatography/Mass Spectrometry in the Profiling of Several Antioxidants in Botanicals", 2014, InTech, Chapter 5, p. 103-133. (Year: 2014).*
Marshall et al., "ORAC Value Change for X14 Lozenge Upon the Addition of Rosemary", May 1, 2013.
Moldoveanu et al., "Analysis of pentacyclic trierpeniod acids in several bioactive botanicals", Jul. 30, 2015.
Moldoveanu et al., "Antioxidant Properties and Chemical Changes in Snus Tobacco Blend upon the Addition of two Botanicals", Mar. 8, 2013.

(Continued)

*Primary Examiner* — Michael J Felton
*Assistant Examiner* — Sonny V Nguyen
(74) *Attorney, Agent, or Firm* — Foley & Lardner LLP

(57) ABSTRACT

Provided are smoking products and methods of preparing smoking products that include tobacco and a deflavored rosemary or a heat-treated rosemary. The deflavored and/or heat-treated rosemary may have been previously heated at a temperature and a time sufficient to reduce or remove flavorant components compared to the use of untreated rosemary. The heated rosemary may include one or more pentacyclic triterpenoid acids such as betulinic, betul-18-enoic, oleanolic, and ursolic acids.

13 Claims, 5 Drawing Sheets

(56) References Cited

OTHER PUBLICATIONS

Moldoveanu et al., "Antioxidant properties of an experimental snus with added rosemary", dated Sep. 4, 2013.
Moldoveanu et al., "Antioxidant properties of green tea and of dry rosemary after heating", Jun. 25, 2013.
Moldoveanu et al., "Decrease upon heating of three flavor compounds in rosemary", Nov. 12, 2015.
Moldoveanu et al., "Profiling for antioxidants in several botanicals", May 17, 2013.
Moldoveanu et al., "Transfer into Cigarette Smoke of four Pentacyclic Triterpenoid acids from cigarettes with 5% added rosemary", Sep. 29, 2015.
International Search Report and Written Opinion in PCT/US2017/019950, dated May 25, 2017, 9 pages.

\* cited by examiner

ROSEMARY IN A TOBACCO BLEND

TECHNOLOGY

The present application is directed to smoking tobacco products or articles, generally, and more specifically to smoking tobacco products that incorporate heat-treated or deflavored rosemary.

BACKGROUND

Through the years, various treatment methods and additives have been proposed for altering the overall character or nature of tobacco materials utilized in tobacco products. For example, additives or treatment processes are sometimes utilized in order to alter the chemistry or sensory properties of the tobacco material, or in the case of smokable tobacco materials, to alter the chemistry or sensory properties of mainstream smoke generated by smoking products including the tobacco material. An example of an additive is a natural botanical (e.g., plant extract), which has been incorporated into both smoking and smokeless tobacco products, such as those disclosed in U.S. Pat. Nos. 4,991,596; 8,434,496; 8,991,403; 8,994,072; 9,155,321; and 9,155,334; and US Publication. Nos. 2015/0068544, US 2015/0068545, and US 2015/0101627.

U.S. Pat. No. 4,991,596 is directed to a smoking article that includes a short, combustible, carbonaceous fuel element in a heat exchange relationship with a substrate carrying glycerin, tobacco extract, and a portion of an essential oil gland bearing plant. For example, fragments of cinnamon bark, lovage root, chamomile flowers or cardamon physically separate from the fuel element provide for a controlled release of a flavor profile during use of the smoking article. Heat provided by the burning fuel element acts to release essential oils from the glands to provide a complex flavor and aroma profile. The smoking article is capable of providing the user with many of the pleasures of smoking by heating but not necessarily burning tobacco.

U.S. Pat. No. 8,434,496 is directed to a method of thermally processing a tobacco material, the method including (i) mixing a tobacco material, water, and an additive selected from the group consisting of lysine, glycine, histidine, alanine, methionine, glutamic acid, aspartic acid, proline, phenylalanine, valine, arginine, di- and trivalent cations, asparaginase, saccharides, phenolic compounds, reducing agents, compounds having a free thiol group, oxidizing agents, oxidation catalysts, plant extracts, and combinations thereof, to form a moist tobacco mixture; (ii) heating the moist tobacco mixture at a temperature of at least about 60° C. to form a heat-treated tobacco mixture; and (iii) incorporating the heat-treated tobacco mixture into a tobacco product. Heat-treated tobacco composition prepared according to the method are also provided, such as heat-treated smokeless tobacco composition comprising a tobacco material, water, flavorant, binder, and filler, the heat-treated smokeless tobacco composition having an acrylamide content of less than about 2000 ppb.

U.S. Pat. No. 8,991,403 is directed to a method of thermally processing a tobacco, the method including the steps of (i) mixing a tobacco material, water, and an additive selected from the group consisting of lysine, glycine, histidine, alanine, methionine, glutamic acid, aspartic acid, proline, phenylalanine, valine, arginine, di- and trivalent cations, asparaginase, saccharides, phenolic compounds, reducing agents, compounds having a free thiol group, oxidizing agents, oxidation catalysts, plant extracts, and combinations thereof, to form a moist tobacco mixture; (ii) heating the moist tobacco mixture at a temperature of at least about 60° C. to form a heat-treated tobacco mixture; and (iii) incorporating the heat-treated tobacco mixture into a tobacco product. Heat-treated tobacco composition prepared according to the method are also provided, such as heat-treated smokeless tobacco composition comprising a tobacco material, water, flavorant, binder, and filler, the heat-treated smokeless tobacco composition having an acrylamide content of less than about 2000 ppb.

U.S. Pat. No. 8,994,072 is directed to a method of preparing a tobacco material for use in a smoking article, including (i) mixing a tobacco material, water, and an additive selected from the group consisting of lysine, glycine, histidine, alanine, methionine, glutamic acid, aspartic acid, proline, phenylalanine, valine, arginine, di- and trivalent cations, asparaginase, saccharides, phenolic compounds, reducing agents, compounds having a free thiol group, oxidizing agents, oxidation catalysts, plant extracts, and combinations thereof; (ii) heating the mixture; and (iii) incorporating the heat-treated mixture into a smoking article as a smokable material. A smoking article in the form of a cigarette is also provided that includes a tobacco material pre-treated to inhibit reaction of asparagine to form acrylamide in mainstream smoke. Upon smoking, the smoking article is characterized by an acrylamide content of mainstream smoke that is reduced relative to an untreated control smoking article.

U.S. Pat. No. 9,155,321 is directed to a meltable smokeless tobacco composition configured for insertion into the mouth of a user. The smokeless tobacco composition includes a tobacco material and a lipid having a melting point of about 36° C. to about 45° C. An associated process is also provided. The process includes melting a lipid having a melting point of about 36° C. to about 45° C. to form a molten lipid composition, mixing a tobacco material with the molten lipid composition to form a molten smokeless tobacco composition, and cooling the molten smokeless tobacco composition to form a solidified smokeless tobacco composition.

U.S. Pat. No. 9,155,334 is directed to a method of modifying the content of certain bacteria in uncured tobacco material, the method including contacting an uncured tobacco material with a treatment solution, wherein the treatment solution is selected from the group consisting of: (i) a solution comprising salt, sugar, or a combination thereof; (ii) a solution comprising one or more enzymes; and (iii) a solution comprising one or more probiotics, wherein said contacting provides a treated tobacco material having a reduced total bacterial content following harvest. In certain embodiments, the treated tobacco material is subsequently cured, and can optionally be fermented. Smoking articles and smokeless tobacco products including such treated tobacco materials are also provided.

US Publication No. 2015/0068544 is directed to a smokeless tobacco product configured for insertion into the mouth of a user of the product, the smokeless tobacco product including a tobacco material mixed with at least one botanical material, wherein the botanical material comprises at least about 0.1% of the total dry weight of the smokeless tobacco product. One exemplary product is in the form of a snus product contained within a water-permeable pouch, which includes at least about 50% of a pasteurized and fermented particulate tobacco material, based on the total dry weight of the smokeless tobacco product, and a botanical material in particulate form.

US Publication No. 2015/0068545 is directed to a smokeless tobacco product configured for insertion into the mouth of a user of the product, the smokeless tobacco product including a dissolvable or meltable base composition admixed with a tobacco material and a botanical material, wherein the botanical material is present in an amount of at least about 0.1% of the total dry weight of the smokeless tobacco product.

US Publication No. 2015/0101627 is directed to a smokeless tobacco pastille configured for insertion into the mouth of a user. The smokeless tobacco pastille may include (i) a tobacco material present in an amount of less than about 40 dry weight percent, based on the total dry weight of the pastille; (ii) at least one natural gum binder present in an amount of at least about 25 dry weight percent; and (iii) a plurality of sugar alcohols present in a total amount of at least about 40 dry weight percent, the predominant component of the plurality of sugar alcohols being isomalt or erythritol, wherein the shape of the smokeless tobacco pastille is moldable in the oral cavity.

Some botanical materials include pentacyclic triterpenoid acids including betulinic acid, oleanolic acid, and ursolic acid, which have been reported to have beneficial health properties such as antiviral and anti-inflammatory properties. Additionally, it has been reported that pentacyclic triterpenoid acids in vitro are capable of inhibiting the development of various cancer cell types. These pentacyclic triterpenoid acids can be found in rosemary. As such, it would be advantageous to have a smoking product that may have the beneficial health properties of rosemary, but which does not significantly alter the taste of the smoking product.

SUMMARY

The present application relates to products and methods of preparing products made or derived from tobacco, or that otherwise incorporate tobacco, that are intended for human consumption.

In one aspect, the smoking product may include tobacco and a deflavored rosemary. In some embodiments, the deflavored rosemary may have been heated at a temperature of about 100° C. to about 200° C. for about 0.5 to about 8 hours. The deflavored rosemary may contain about 50 wt % to about 99 wt % less 1,8-cineole, camphor, and borneol after heating compared to rosemary prior to heating. In some embodiments, the deflavored rosemary may include one or more pentacyclic triterpenoid acids such as betulinic acid, oleanolic acid, ursolic acid, and betul-18-enoic acid. The deflavored rosemary may contain no less than about 75 wt % of the pentacyclic triterpenoid acids after heating compared to before heating. In some embodiments, the smoking product may include about 1 wt % to about 10 wt % of the deflavored rosemary.

In another aspect, the smoking product may include tobacco and heat-treated rosemary. The heat-treated rosemary may have been heated at a temperature and a time sufficient to reduce or remove aromatic and/or flavorant components of the rosemary when compared to an untreated rosemary. In some embodiments, the heat-treated rosemary may have been heated at a temperature of about 100° C. to about 200° C. for about 0.5 to about 8 hours. The heat-treated rosemary may contain about 50 wt % to about 99 wt % less 1,8-cineole, camphor, and borneol compared to the untreated rosemary. In some embodiments, the heat-treated rosemary may include one or more pentacyclic triterpenoid acids such as betulinic acid, oleanolic acid, ursolic acid, and betul-18-enoic acid. The heat-treated rosemary may contain no less than about 75 wt % of the pentacyclic triterpenoid acids present in the untreated rosemary. In some embodiments, the smoking product may include about 1 wt % to about 10 wt % of the heat-treated rosemary.

In another aspect, the present technology provides a method of preparing a smoking product including blending tobacco and heat-treated rosemary, wherein the heat-treated rosemary has been previously heated at a temperature and a time sufficient to reduce or remove flavorant components compared to the untreated rosemary.

DETAILED DESCRIPTION

Figure 1:
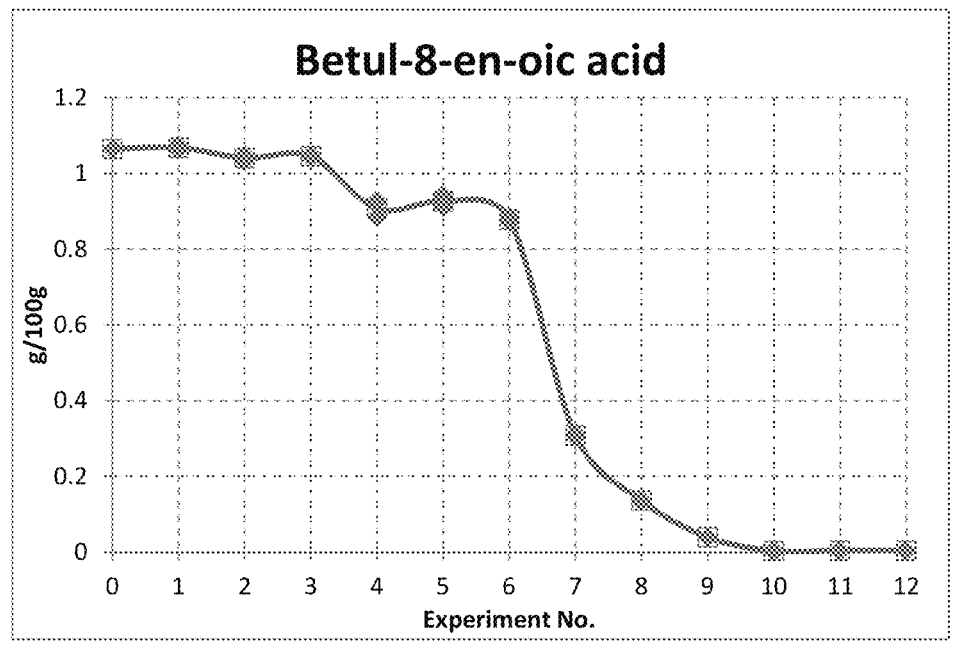
FIG. 1 illustrates the variation in the level of betul-8-enoic acid for different heating experiments (g acid/100 g rosemary), according to some embodiments.

As used herein, rosemary refers to the botanical material *Rosmarinus officinalis* commonly known as rosemary, but does not include rosemary extracts, such as oils, aqueous extracts, or organic solvent extracts (e.g., ethanol). Rosemary is a woody, perennial herb with fragrant, evergreen, needle-like leaves and white, pink, purple, or blue flowers, native to the Mediterranean region and Asia. Rosemary is a member of the mint family Lamiaceae. Rosemary leaves are often used as flavoring in foods and rosemary oil extract is often used in fragrant bodily perfumes, shampoos, cleaning products, or to emit aroma into a room. Rosemary includes compounds from various classes that may provide certain bioactive effects, such as phytochemical s.

The rosemary may be any natural part derived from a rosemary plant (e.g., leaf, stem, flower, etc.). In some embodiments, the rosemary is rosemary leaf. In some embodiments, the rosemary may be fresh or frozen. In some embodiments, the rosemary may have been previously dried using any known method (e.g., freeze drying, dehydration, air drying, or heat drying at a temperature below 100° C.).

In some embodiments, the rosemary may be in shredded or particulate (e.g., a milled or ground form characterized as granular or powder) form. In some embodiments, the rosemary may be rosemary that has not been shredded, milled, or ground. In some embodiments, the rosemary may be intact rosemary leaves (i.e., whole rosemary leaves). The rosemary may be harvested using any known method including summer or winter harvesting, harvesting rosemary that is not more than 10 years old, drying the rosemary on or off the stem, etc. The use of rosemary in tobacco-related applications is discussed, for example, in US Publication No. 2015/0101627, US Publication No. 2015/0068545 and US Publication No. 20150068544.

In one aspect, the smoking product of the present technology includes tobacco and deflavored rosemary. In some embodiments, the smoking product may be a cigarette. In some embodiments, the smoking product may be a cigar. In some embodiments, the smoking product may be a composition for use in a pipe.

In some embodiments, the deflavored rosemary may have been heated at a temperature of about 100° C. to about 200° C. for about 0.5 to about 8 hours. In another embodiment, the deflavored rosemary may have been heated at a temperature of about 125° C. to about 175° C. for about 0.5 to about 6 hours. In some embodiments, the deflavored rosemary may have been heated at a temperature of about 140° C. to about 160° C. for about 1 to about 4 hours. In some embodiments, the deflavored rosemary may have been heated at a temperature of about 160° C. to about 180° C. for about 0.5 to about 2 hours. In some embodiments, the deflavored rosemary may be heated one or more days before being combined with the tobacco. In some embodiments, the deflavored rosemary may be heated one or more months before being combined with the tobacco.

In some embodiments, the tobacco and/or deflavored rosemary may include other tobacco additives. In some embodiments, the tobacco and/or deflavored rosemary may include casing and/or top dressing components. In some embodiments, the tobacco and deflavored rosemary may be treated with tobacco additives after being combined together. In some embodiments, the tobacco may be treated with tobacco additives before being combined with the deflavored rosemary. In some embodiments, the deflavored rosemary may be treated with tobacco additives before being combined with the tobacco. In some embodiments, the tobacco additives may be the same for the tobacco and deflavored rosemary. In some embodiments, the tobacco additives may be different for the tobacco and deflavored rosemary.

As used herein, flavor is the sensory impression of food, drink, or other substances that is determined primarily by the chemical senses of taste and/or smell.

Accordingly, as used herein, deflavored rosemary refers to a treated rosemary that does not significantly alter the flavor of a smoking product due to components found in rosemary prior to being treated. Deflavoring of the rosemary may be accomplished through reduction, or elimination, of one or more of the plant's naturally occurring flavor components including, but not limited to, eucalyptol (i.e., 1,8-cineol), camphor, borneol, o-cymene, linalool, bornyl acetate, caryophyllene, alpha-terpineol, humulene, 4,6,6-trimethylbicyclo[3.1.1]hept-3-en-2-one, and α,α-dimethyl-4-methylenecyclohexanemethanol. Deflavored rosemary would be reduced in the concentration of one or more of these same components when compared to the untreated rosemary. In some embodiments, the flavor components that are reduced in the deflavored rosemary may include eucalyptol (i.e., 1,8-cineol), camphor, borneol, and combinations thereof.

The deflavored rosemary may contain less than about 2.5 wt % carnosic acid. In some embodiments, the deflavored rosemary may contain less than about 2 wt % carnosic acid. In some embodiments, the deflavored rosemary may contain less than about 1 wt % carnosic acid. In some embodiments, the deflavored rosemary may contain less than about 0.5 wt % carnosic acid.

The deflavored rosemary may contain less than about 1.5 wt % of rosmarinic acid. In some embodiments, the deflavored rosemary may contain less than about 1.2 wt % of rosmarinic acid. In some embodiments, the deflavored rosemary may contain less than about 1.0 wt % of rosmarinic acid.

The deflavored rosemary may contain about 20 wt % to about 50 wt % less carnosic acid and rosmarinic acid after heating compared to before heating. In some embodiments, the deflavored rosemary may contain about 25 wt % less carnosic acid and rosmarinic acid after heating compared to before heating. In some embodiments, the deflavored rosemary may contain about 30-50 wt % less carnosic acid and about 25-35 wt % less rosmarinic acid after heating compared to before heating.

The deflavored rosemary may contain less than about 0.5 wt % of 1,8-cineole. In some embodiments, the deflavored rosemary may contain less than about 0.3 wt % of 1,8-cineole. In some embodiments, the deflavored rosemary may contain less than about 0.1 wt % of 1,8-cineole. In some embodiments, the deflavored rosemary may contain less than about 0.05 wt % of 1,8-cineole.

The deflavored rosemary may contain less than about 0.2 wt % of camphor. In some embodiments, the deflavored rosemary may contain less than about 0.1 wt % of camphor. In some embodiments, the deflavored rosemary may contain less than about 0.05 wt % of camphor.

The deflavored rosemary may contain less than about 0.2 wt % of borneol. In some embodiments, the deflavored rosemary may contain less than about 0.1 wt % of borneol. In some embodiments, the deflavored rosemary may contain less than about 0.05 wt % of borneol.

The deflavored rosemary may contain about 50 wt % to about 99 wt % less 1,8-cineole, camphor, and borneol after heating compared to before heating. In some embodiments, the deflavored rosemary may contain about 80 wt % to about 95 wt % less 1,8-cineole, camphor, and borneol after heating compared to before heating. In some embodiments, the deflavored rosemary may contain about 90-99 wt % less 1,8-cineole, about 85-95 wt % less camphor, and about 85-95 wt % less borneol after heating compared to before heating.

The deflavored rosemary may include one or more pentacyclic triterpenoid acids. The pentacyclic triterpenoid acids may include, but are not limited to, betulinic acid, oleanolic acid, ursolic acid, betul-18-enoic acid (i.e., (3β)-3-hydroxy-lupa-18,20(29)-diene-28-oic acid), and combinations thereof. In some embodiments, the deflavored rosemary may contain no less than about 50 wt % of the pentacyclic triterpenoid acids after heating compared to before heating. In some embodiments, the deflavored rosemary may contain no less than about 65 wt % of the pentacyclic triterpenoid acids after heating compared to before heating. In some embodiments, the deflavored rosemary may contain no less than about 75 wt % of the pentacyclic triterpenoid acids after heating compared to before heating. In some embodiments, the deflavored rosemary may contain about 75 wt % to about 90 wt % of the pentacyclic triterpenoid acids after heating compared to before heating.

The smoking product may include about 1 wt % to about 20 wt % of the deflavored rosemary, 1 wt % to about 10 wt % of the deflavored rosemary, about 1 wt % to about 5 wt % of the deflavored rosemary, or about 0.5 wt % to about 2 wt % of the deflavored rosemary. In some embodiments, the smoking product may include about 1 wt % to about 10 wt % of the deflavored rosemary. In some embodiments, the smoking product may include about 1 wt % to about 5 wt % of the deflavored rosemary.

The smoking product may include about 80 wt % to about 99 wt % tobacco, 90 wt % to about 99 wt % tobacco, about 95 wt % to about 99 wt % tobacco, or about 95 wt % to about 99.5 wt % tobacco. In some embodiments, the smoking product may include about 80 wt % to about 99 wt % tobacco. In some embodiments, the smoking product may include about 90 wt % to about 99 wt % tobacco. In some embodiments, the smoking product may include about 95 wt % to about 99 wt % tobacco.

The smoking product of the present technology includes tobacco and heat-treated rosemary. In some embodiments, the smoking product may be a cigarette. In some embodiments, the smoking product may be a cigar. In some embodiments, the smoking product may be a composition for use in a pipe.

The heat-treated rosemary may have been heated at a temperature of about 100° C. to about 200° C. for about 0.5 to about 8 hours. In some embodiments, the heat-treated rosemary may have been heated at a temperature of about 125° C. to about 175° C. for about 0.5 to about 8 hours. In some embodiments, the heat-treated rosemary may have been heated at a temperature of about 140° C. to about 160° C. for about 1 to about 4 hours. In some embodiments, the heat-treated rosemary may have been heated at a temperature of about 160° C. to about 180° C. for about 0.5 to about 2 hours. In some embodiments, the heat-treated rosemary may be heated one or more days before being combined with the tobacco. In some embodiments, the heat-treated rosemary may be heated one or more months before being combined with the tobacco.

The tobacco and/or heat-treated rosemary may include other tobacco additives. In some embodiments, the tobacco and/or heat-treated rosemary may include casing and/or top dressing components. In some embodiments, the tobacco and heat-treated rosemary may be treated with tobacco additives after being combined together. In some embodiments, the tobacco may be treated with tobacco additives before being combined with the heat-treated rosemary. In some embodiments, the heat-treated rosemary may be treated with tobacco additives before being combined with the tobacco. In some embodiments, the tobacco additives may be the same for the tobacco and heat-treated rosemary. In some embodiments, the tobacco additives may be different for the tobacco and heat-treated rosemary.

The heat-treated rosemary may contain less than about 2.5 wt % carnosic acid. In some embodiments, the heat-treated rosemary may contain less than about 2 wt % carnosic acid. In some embodiments, the heat-treated rosemary may contain less than about 1 wt % carnosic acid. In some embodiments, the heat-treated rosemary may contain less than about 0.5 wt % carnosic acid.

The heat-treated rosemary may contain less than about 1.5 wt % of rosmarinic acid. In some embodiments, the heat-treated rosemary may contain less than about 1.2 wt % of rosmarinic acid. In some embodiments, the heat-treated rosemary may contain less than about 1.0 wt % of rosmarinic acid.

The heat-treated rosemary may contain about 20 wt % to about 50 wt % less carnosic acid and rosmarinic acid compared to the untreated rosemary. In some embodiments, the heat-treated rosemary may contain about 25 wt % less carnosic acid and rosmarinic acid compared to the untreated rosemary. In some embodiments, the heat-treated rosemary may contain about 30-50 wt % less carnosic acid and about 25-35 wt % less rosmarinic acid compared to the untreated rosemary.

The heat-treated rosemary may contain less than about 0.5 wt % of 1,8-cineole. In some embodiments, the heat-treated rosemary may contain less than about 0.3 wt % of 1,8-cineole. In some embodiments, the heat-treated rosemary may contain less than about 0.1 wt % of 1,8-cineole. In some embodiments, the heat-treated rosemary may contain less than about 0.05 wt % of 1,8-cineole.

The heat-treated rosemary may contain less than about 0.2 wt % of camphor. In some embodiments, the heat-treated rosemary may contain less than about 0.1 wt % of camphor. In some embodiments, the heat-treated rosemary may contain less than about 0.05 wt % of camphor.

The heat-treated rosemary may contain less than about 0.2 wt % of borneol. In some embodiments, the heat-treated d rosemary may contain less than about 0.1 wt % of borneol. In some embodiments, the heat-treated rosemary may contain less than about 0.05 wt % of borneol.

The heat-treated rosemary may contain about 50 wt % to about 99 wt % less 1,8-cineole, camphor, and borneol compared to the untreated rosemary. In some embodiments, the heat-treated rosemary may contain about 80 wt % to about 95 wt % less 1,8-cineole, camphor, and borneol compared to the untreated rosemary. In some embodiments, the heat-treated rosemary may contain about 90-99 wt % less 1,8-cineole, about 85-95 wt % less camphor, and about 85-95 wt % less borneol compared to the untreated rosemary.

The heat-treated rosemary may include one or more pentacyclic triterpenoid acids. The pentacyclic triterpenoid acids may include, but are not limited to, betulinic acid, oleanolic acid, ursolic acid, betul-18-enoic acid, and combinations thereof. In some embodiments, the heat-treated rosemary may contain no less than about 50 wt % of the pentacyclic triterpenoid acids after heating compared to before heating. In some embodiments, the heat-treated rosemary may contain no less than about 65 wt % of the pentacyclic triterpenoid acids after heating compared to before heating. In some embodiments, the heat-treated rosemary may contain no less than about 75 wt % of the pentacyclic triterpenoid acids after heating compared to before heating. In some embodiments, the deflavored rosemary may contain about 75 wt % to about 90 wt % of the pentacyclic triterpenoid acids after heating compared to before heating.

The smoking product may include about 1 wt % to about 20 wt % of the heat-treated rosemary, 1 wt % to about 10 wt % of the heat-treated rosemary, about 1 wt % to about 5 wt % of the deflavored rosemary, or about 0.5 wt % to about 2 wt % of the heat-treated rosemary. In some embodiments, the smoking product may include about 1 wt % to about 10 wt % of the heat-treated rosemary. In some embodiments, the smoking product may include about 1 wt % to about 5 wt % of the heat-treated rosemary.

The smoking product may include about 80 wt % to about 99 wt % tobacco, 90 wt % to about 99 wt % tobacco, about 95 wt % to about 99 wt % tobacco, or about 95 wt % to about 99.5 wt % tobacco. In some embodiments, the smoking product may include about 80 wt % to about 99 wt % tobacco. In some embodiments, the smoking product may include about 90 wt % to about 99 wt % tobacco. In some embodiments, the smoking product may include about 95 wt % to about 99 wt % tobacco.

In another aspect, the present technology provides a method of preparing a smoking tobacco product.

In one aspect, the method may include blending or mixing the tobacco and the deflavored rosemary described herein. In some embodiments, the deflavored rosemary may be cut, heated, and blended with the tobacco. In some embodiments, the deflavored rosemary may be cut, heated, blended, and rolled into a form of a string. In some embodiments, the deflavored rosemary may be cut, heated, blended with tobacco, and rolled into a form of a string. In some embodiments, the string may be arranged linearly along the length of a smoking product, such as a cigarette or cigar, that includes tobacco. In some embodiments, the string may be arranged linearly along the length of a tobacco rod. In another embodiment, the string may be coiled. In some embodiments, the smoking product may include one or more strings of the deflavored rosemary and/or the deflavored rosemary and tobacco.

The tobacco and/or deflavored rosemary may be treated with tobacco additives (e.g. casing and/or top dressing components). In some embodiments, the tobacco and deflavored rosemary may be treated with tobacco additives after being combined together. In some embodiments, the tobacco may be treated with tobacco additives before being combined with the deflavored rosemary. In some embodiments, the tobacco additives may be the same for both the tobacco and deflavored rosemary. In some embodiments, the tobacco additives may be different for the tobacco and deflavored rosemary.

The tobacco and deflavored rosemary may be processed into a tobacco rod. In some embodiments, the tobacco and deflavored rosemary may be processed into a cigar.

In another aspect, the method may include blending tobacco and a heat-treated rosemary as described herein, wherein the heat-treated rosemary has been previously heated at a temperature and a time sufficient to reduce or remove flavorant components compared to the untreated rosemary.

In one aspect, the method may include blending or mixing the tobacco and the heat-treated rosemary described herein.

In one aspect, the method may include blending or mixing the tobacco and the heat-treated rosemary described herein. In some embodiments, the heat-treated rosemary may be cut, heated, and blended with the tobacco. In some embodiments, the heat-treated rosemary may be cut, heated, blended, and rolled in to a form of a string. In some embodiments, the heat-treated rosemary may be cut, heated, blended with tobacco, and rolled in to a form of a string. In some embodiments, the string may be arranged linearly along the length of a smoking product, such as a cigarette or cigar, that includes tobacco. In some embodiments, the string may be arranged linearly along the length of a tobacco rod. In another embodiment, the string may be coiled. In some embodiments, the smoking product may include one or more strings of the heat-treated rosemary and/or the heat-treated rosemary and tobacco.

The tobacco and/or heat-treated rosemary may be treated with tobacco additives (e.g. casing and/or top dressing components). In some embodiments, the tobacco and heat-treated rosemary may be treated with tobacco additives after being combined together. In some embodiments, the tobacco may be treated with tobacco additives before being combined with the heat-treated rosemary. In some embodiments, the tobacco and heat-treated rosemary may be treated with tobacco additives before being combined together. In some embodiments, the tobacco additives may be the same for both the tobacco and heat-treated rosemary. In some embodiments, the tobacco additives may be different for the tobacco and heat-treated rosemary.

The tobacco and heat-treated rosemary may be processed into a tobacco rod. In some embodiments, the tobacco and heat-treated rosemary may be processed into a cigar.

In some embodiments, the smoking products described herein may reduce or possibly prevent the incidence or effects of viruses, inflammations, or cancers. In some embodiments, the cancers may be those associated with smoking.

The smoking products described herein may be an object or device such as a cigarette or pipe which is lit and smoked by a smoker. Smoking products may include, but are not limited to, plain and filter cigarettes, pipes, cigars, cheroots, and the like. In some embodiments, the smoking product may be a cigarette. In some embodiments, the cigarette may be a filter cigarette. The filter cigarette may include a cylindrical filter element aligned in an end-to-end relationship with a substantially cylindrical rod shaped structure that includes tobacco and the deflavored or heat-treated rosemary (i.e., a tobacco rod). The filter element may include plasticized cellulose acetate tow circumscribed by a paper material known as "plug wrap." Certain filter elements can incorporate polyhydric alcohols. Typically, the filter element is attached to one end of the tobacco rod using a circumscribing wrapping material known as "tipping paper." The tipping material and plug wrap may be perforated, in order to provide dilution of drawn mainstream smoke with ambient air. Descriptions of cigarettes and the various components thereof are set forth in *Tobacco Production, Chemistry and Technology*, Davis et al. (Eds.) (1999).

A cigarette is employed by a smoker by lighting one end thereof and burning the tobacco rod. The heat generated by the burning end of a cigarette, will gradually permeate along the length of the tobacco rod. The resulting increase in temperature, will allow or cause substances or compositions to be progressively released. As a result, upon a smoker using his/her mouth to draw on the opposite end (e.g., the filter end) of the cigarette, smoke with at least some of these substances or compositions will be carried into the mouth, throat, and/or lungs of the smoker and thereby cause the substance or composition to be ingested by the smoker. The same process similarly applies to all smoking products upon lighting and burning of the tobacco and deflavored or heat-treated rosemary. In some embodiments, the substances or compositions include, but are not limited to, pentacyclic triterpenoid acids. In some embodiments, the pentacyclic triterpenoid acids may include betulinic acid, oleanolic acid, ursolic acid, betul-18-enoic acid, and combinations thereof.

Tobacco materials (i.e., tobacco) as used herein can be derived from various types of tobacco such as flue-cured tobacco, burley tobacco, Oriental tobacco, Maryland tobacco, dark tobacco including dark air cured tobacco and dark-fired tobacco, *Rustica* tobacco, other more rare or specialty tobaccos, and blends thereof. The tobacco may also include reconstituted tobacco materials. Often, the tobaccos are those that have been appropriately cured and aged.

In some embodiments, tobacco material for cigarettes may be used in blended forms. For example, certain popular tobacco blends, commonly referred to as "American blends," include mixtures of flue-cured tobacco, burley tobacco and Oriental tobacco, and in many cases, certain processed tobaccos, such as reconstituted tobacco and processed tobacco stems. The precise amount of each type of tobacco within a tobacco blend used for the manufacture of a particular cigarette brand varies from brand to brand. However, for many tobacco blends, flue-cured tobacco makes up a relatively large proportion of the blend, while Oriental tobacco makes up a relatively small proportion of the blend. See, for example, *Tobacco Encyclopedia*, Voges (Ed.) p. 44-45 (1984), Browne, *The Design of Cigarettes*, 3rd Ed., p. 43 (1990) and *Tobacco Production, Chemistry and Technology*, Davis et al. (Eds.) p. 346 (1999). Tobacco blends may contain tobacco materials that have processed forms, such as processed tobacco stems (e.g., cut-rolled stems, cut-rolled-expanded stems or cut-puffed stems), volume expanded tobacco (e.g., puffed tobacco, such as dry ice expanded tobacco (DIET), preferably in cut filter form). Tobacco materials also can have the form of reconstituted tobaccos (e.g., reconstituted tobaccos manufactured using paper-making type or cast sheet type processes). Tobacco reconstitution processes traditionally convert portions of tobacco that nominally might be wasted into commercially useful forms. For example, tobacco stems, recyclable pieces of tobacco and tobacco dust can be used to manufacture processed reconstituted tobaccos of fairly uniform consistency. See, for example, *Tobacco Encyclopedia*, Voges (Ed.) p. 44-45 (1984), Browne, The Design of Cigarettes, 3rd Ed., p. 43 (1990) and *Tobacco Production, Chemistry and Technology*, Davis et al. (Eds.) p. 346 (1999). Various representative tobacco types, processed types of tobaccos, types of tobacco blends, cigarette components and ingredients, and tobacco rod configurations, also are set forth in U.S. Pat. No. 4,836,224 to Lawson et al.; U.S. Pat. No. 4,924,883 to Perfetti et al.; U.S. Pat. No. 4,924,888 to Perfetti et al.; U.S. Pat. No. 5,056,537 to Brown et al.; U.S. Pat. No. 5,159,942 to Brinkley et al.: U.S. Pat. No. 5,220,930 to Gentry: U.S. Pat. No. 5,360,023 to Blakley et al.; U.S. Pat. No. 5,714,844 to Young et al.; U.S. Pat. No. 6,730,832 to Dominguez et al.; U.S. Pat. No. 6,701,936 to Shafer et al.; and U.S. Pat. No. 7,900,639 to Perfetti et al.; U.S. Patent Application Publication Nos. 2003/0075193 to Li et al.; 2003/0131859 to Li et al.; 2004/0084056 to Lawson et al.; 2004/0255965 to Perfetti et al.; 2005/0066984 to Crooks et al.: and 2005/0066986 to Nestor et al.; PCT WO 02/37990 to Bereman; and Bombick et al., *Fund. Appl. Toxicol.*, 39, p. 11-17 (1997); all of which are incorporated herein by reference.

The tobacco materials may be used in forms, and in manners, that are traditional for the manufacture of smoking products such as cigarettes. The tobacco for cigarette blends normally is used in cut filler form (e.g., shreds or strands of tobacco filler cut into widths of about 1/10 inch to about 1/60 inch or about 1/20 inch to about 1/35 inch, and in lengths of about 1/4 inch to about 3 inches). The amount of tobacco filler used within the tobacco rod of a cigarette may range from about 0.6 g to about 1 g. The tobacco filler may be employed so as to fill the tobacco rod of a cigarette at a packing density of about 100 mg/cm$^3$ to about 300 mg/cm$^3$ or about 150 mg/cm$^3$ to about 275 mg/cm$^3$.

The wrapping material of the tobacco rod can have a wide range of compositions and properties. The selection of a particular wrapping material will be readily apparent to those skilled in the art of cigarette design and manufacture. Tobacco rods can have one layer of wrapping material; or tobacco rods can have more than one layer of circumscribing wrapping material, such as is the case for the so-called "double wrap" tobacco rods. Exemplary types of wrapping materials, wrapping material components, and treated wrapping materials are described in U.S. Pat. No. 5,220,930 to Gentry; and U.S. patent application Ser. No. 10/303,648, filed Nov. 25, 2002; Ser. No. 10/324,418, filed Dec. 20, 2002, and Ser. No. 10/440,290, filed May 16, 2003; which are incorporated herein by reference in their entireties.

The filter element may vary in the present technology. As described in U.S. Pat. No. 8,186,360 to Marshall et al. (incorporated herein by reference), the filter may include one or more segments of filter material capable of filtration of solid products and/or vapor phase components of mainstream smoke generated after the lighting and upon a smoker using his/her mouth to draw on the filter end of the cigarette. In some embodiments, the filter may include an adsorbent material located within a central compartment between two sections of filter material. The first filter segment and second filter segment can include various types of filter material (e.g., cellulose acetate tow impregnated with plasticizer, such as triacetin). If desired, the filter element also can be incorporate other components that have the ability to alter the properties of the mainstream smoke that passes throughout the filter element. See, for example, U.S. Patent Publication Nos. 2004/0237984 to Figlar et al.; 2005/0066982 to Clark et al.; 2005/0268925 to Schluter et al.; 2006/0130861 to Luan et al.; and 2006/0174899 to Luan et al., which are incorporated herein by reference. Other filter element arrangements could be used without departing from the present technology. For example, the adsorbent material could be dispersed within one or more sections of filter material as opposed to placement in a central cavity or compartment. Typically, the filter element includes 1 to 6 segments, frequently 2 to 4 segments. Other representative filter element components and designs are described in Browne, *The Design of Cigarettes*, 3$^{rd}$ Ed. (1990); *Tobacco Production, Chemistry and Technology*, Davis et al. (Eds.) 1999; U.S. Pat. No. 4,508,525 to Berger; U.S. Pat. No. 4,920,990 to Lawrence et al.; U.S. Pat. No. 5,101,839 to Jakob et al.; U.S. Pat. No. 5,105,834 to Saintsing et al.; U.S. Pat. No. 5,105,838 to White et al.; and U.S. Pat. No. 5,360,023 to Blakley et al.; U.S. Patent Application 2002/0166563; and European Patent No. 920816.

The filter material used in the filter segments of the filter element can vary, and can be any material of the type that can be employed as a tobacco smoke filter for cigarettes. Preferably, a traditional cigarette filter material is used, such as cellulose acetate tow, gathered cellulose acetate web, polypropylene tow, gathered cellulose acetate web, gathered paper, strands of reconstituted tobacco, or the like. The filter material may be filamentary or fibrous tow such as cellulose acetate, polyolefins such as polypropylene, or the like. One filter material that may provide a suitable filter rod is cellulose acetate tow having 3 denier per filament and 40,000 total denier. Cellulose acetate tow having 3 denier per filament and 35,000 total denier can also provide a suitable filter rod. As another example, cellulose acetate tow having 8 denier per filament and 40,000 total denier can provide a suitable filter rod. For further examples, see the types of filter materials as set forth in U.S. Pat. No. 3,424,172 to Neurath; U.S. Pat. No. 4,811,745 to Cohen et al.; U.S. Pat. No. 4,925,602 to Hill et al.; U.S. Pat. No. 5,225,277 to Takegawa et al. and U.S. Pat. No. 5,271,419 to Arzonico et al.; each of which is incorporated herein by reference.

The particulate removal efficiency of each segment of filter material in the filter element can vary. For fibrous filter materials, particulate removal efficiency is preferably quantified in terms of weight per unit length of the filaments forming the fibers. Exemplary filter materials exhibit a filtration efficiency of about 1.8 to about 10 denier per filament. Each filter segment in a multi-segment filter element can have the same or different filtration efficiency. In one embodiment, the section of filter material proximal to the tobacco rod has a higher particulate removal efficiency than the section of filter material distal from the tobacco rod. For example, the filaments of the tobacco end section of filter material can have a lower weight per unit length than the filaments of the mouth end section of the filter material. Exemplary filaments for use in the tobacco end section of filter material 38 have a weight per unit length of less than about 2.5 denier per filament, preferably about 1.8 to about 2.5. Exemplary filaments for use in the mouth end section of filter material 36 have a weight per unit length of greater than about 3.0 denier per filament, preferably about 3.0 to about 10.0.

In some embodiments, a plasticizer such as triacetin or carbowax is applied to the filamentary tow in traditional amounts using known techniques. In one embodiment, the plasticizer component of the filter material comprises triacetin and carbowax in a 1:1 ratio by weight. The total amount of plasticizer may be about 4 to about 20 percent by weight, or about 6 to about 12 percent by weight. Other suitable materials or additives used in connection with the construction of the filter element will be readily apparent to those skilled in the art of cigarette filter design and manufacture. See, for example, U.S. Pat. No. 5,387,285 to Rivers, which is incorporated herein by reference.

Upon a smoker using his/her mouth to draw on the filter end of the cigarette, certain amounts of gaseous components of the mainstream smoke are removed from the mainstream smoke by the adsorbent within the filter element. Filters incorporating adsorbent materials, such as carbonaceous filter components (e.g., activated charcoal products), have the capability of capturing a wide range of mainstream tobacco smoke vapor phase components. The adsorbent material can be a material with relatively high surface area capable of adsorbing smoke constituents without a high degree of specificity, or a material that adsorbs certain compounds with a greater degree of specificity, such as an ion exchange resin. Exemplary types of adsorbent include activated carbon, molecular sieves (e.g., zeolites and carbon molecular sieves), clays, ion exchange resins, activated aluminas, silica gels, meerschaum, and mixtures thereof. Any adsorbent material, or mixture of materials, that has the ability to alter the character or nature of mainstream smoke passing through the filter element may be used so long as at least some of the one or more pentacyclic triterpenoid acids are allowed to pass through the filter element.

Typically, the amount of adsorbent within the filter element is at least about 20 mg, often at least about 30 mg, and frequently at least about 40 mg, on a dry weight basis. Typically, the amount of carbonaceous material or other adsorbent within the filter element does not exceed about 500 mg, generally does not exceed about 400 mg, often does not exceed about 300 mg, and frequently does not exceed about 200 mg, on a dry weight basis.

In some embodiments, the adsorbent is a carbonaceous material, which is a material that is composed primarily of carbon, and preferred carbonaceous materials are composed of virtually all carbon. Typically, carbonaceous materials include carbon in amounts of more than about 85 percent, generally more than about 90 percent, often more than about 95 percent, and frequently more than about 98 percent, by weight. The carbonaceous material can have the form of charcoal, but most preferably is an activated carbon material. Activated carbon materials are high surface area materials. Exemplary activated carbon materials have surface areas of more than about 200 $m^2/g$, often more than about 1000 $m^2/g$, and frequently more than about 1500 $m^2/g$. as determined using the Brunaver. Emmel and Teller (BET) method described in J. Amer. Chem. Soc., Vol. 60(2), pp. 309-319 (1938).

The carbonaceous material and/or other adsorbent of the filter element is employed in a suitable form. For example, the carbonaceous material or other adsorbent can have a form that can be characterized as powdered, granular, particulate form, or the like. Typical average product sizes are greater than about 10 Mesh, often greater than about 20 Mesh, and frequently greater than about 30 Mesh. Typical product sizes are less than about 400 Mesh, often less than about 300 Mesh, and frequently less than about 200 Mesh. The terms "granular" and "particulate" are intended to encompass both non-spherical shaped products and spherical products, such as so-called "beaded carbon" described in WO 03/059096, which is incorporated by reference herein.

The carbonaceous materials can be derived from synthetic or natural sources. Materials such as rayon or nylon can be carbonized, followed by treatment with oxygen to provide activated carbonaceous materials. Materials such as wood and coconut shells can be carbonized, followed by treatment with oxygen to provide activated carbonaceous materials. The level of activity of the carbon may vary. Typically, the carbon has an activity of about 60 to about 150 Carbon Tetrachloride Activity (i.e., wt % pickup of carbon tetrachloride). Preferred carbonaceous materials are provided by carbonizing or pyrolyzing bituminous coal, tobacco material, softwood pulp, hardwood pulp, coconut shells, almond shells, grape seeds, walnut shells, macadamia shells, kapok fibers, cotton fibers, cotton linters, and the like. Examples of suitable carbonaceous materials are activated coconut hull based carbons available from Calgon Corp. as PCB and GRC-11 or from PICA as G277, coal-based carbons available from Calgon Corp. as S-Sorb, Sorbite, BPL, CRC-11F, FCA and SGL, wood-based carbons available from Westvaco as WV-B, SA-20 and BSA-20, carbonaceous materials available from Calgon Corp. such as HMC, ASC/GR-1 and SC II, Witco Carbon No. 637, and AMBERSORB 572 or AMBERSORB 563 resins available from Rohm and Haas. Other carbonaceous materials are described in U.S. Pat. No. 4,771,795 to White, et al. and U.S. Pat. No. 5,027,837 to Clearman, et al.; and European Patent Application Nos. 236,922; 419,733; and 419,981.

In some embodiments, the carbonaceous materials are coconut shell types of activated carbons available from sources such as Calgon Carbon Corporation, Gowrishankar Chemicals, Carbon Activated Corp., and General Carbon Corp. See, also, for example, Activated Carbon Compendium, Marsh (Ed.) (2001), which is incorporated herein by reference.

Certain carbonaceous materials can be impregnated with substances, such as transition metals (e.g., silver, gold, copper, platinum, and palladium), potassium bicarbonate, tobacco extracts, polyethyleneimine, manganese dioxide, eugenol, and 4-ketononanoic acid. The carbon composition may also include one or more fillers, such as semolina. Grape seed extracts may also be incorporated into the filter element as a free radical scavenger.

Various types of charcoals and activated carbon materials suitable for incorporation into cigarette filters, various other filter element component materials, various types of cigarette filter element configurations and formats, and various manners and methods for incorporating carbonaceous materials into cigarette filter elements, are set forth in U.S. Pat. No. 2,881,770 to Touey; U.S. Pat. No. 3,101,723 to Seligman et al.; U.S. Pat. No. 3,217,715 to Berger et al.; U.S. Pat. No. 3,236,244 to Irby et al.; U.S. Pat. No. 3,311,519 to Touey et al.; U.S. Pat. No. 3,347,247 to Lloyd; U.S. Pat. No. 3,349,780 to Sublett et al.; U.S. Pat. No. 3,370,595 to Davis et al.; U.S. Pat. No. 3,413,982 to Sublett et al.; U.S. Pat. No. 3,602,231 to Dock; U.S. Pat. No. 3,648,711 to Berger et al.; U.S. Pat. No. 3,957,563 to Sexstone; U.S. Pat. No. 3,972,335 to Tigglebeck et al.; U.S. Pat. No. 4,174,720 to Hall; U.S. Pat. No. 4,201,234 to Neukonun; U.S. Pat. No. 4,223,597 to Lebert; U.S. Pat. No. 5,137,034 to Perfetti et al.; U.S. Pat. No. 5,360,023 to Blakley et al.; U.S. Pat. No. 5,568,819 to Gentry et al.; U.S. Pat. No. 5,622,190 to Arterbery et al.; U.S. Pat. No. 6,537,186 to Veluz; U.S. Pat. No. 6,584,979 to Xue et al.; U.S. Pat. No. 6,761,174 to Jupe et al.; U.S. Pat. No. 6,789,547 to Paine III; and U.S. Pat. No. 6,789,548 to Bereman; U.S. Patent Appl. Pub. Nos. 2002/0166563 to Jupe et al.; 2002/0020420 to Xue et al.; 2003/0200973 to Xue et al.; 2003/0154993 to Paine et al.; 2003/0168070 to Xue et al.; 2004/0194792 to Zhuang et al.; 2004/0226569 to Yang et al.; 2004/0237984 to Figlar et al.; 2005/0133051 to Luau et al.; 2005/0049128 to Buhl et al.; 2005/0066984 to Crooks et al.; 2006/0144410 to Luan et al.; and 2006/0180164 to Paine, III et al.; U.S. patent application Ser. No. 11/226,932 to Coleman, III et al.; European Patent Appl. 579410 to White; PCT WO 2006/051422 to Jupe et al.; and PCT WO 2006/064371 to Banerjea et al.; which are incorporated herein by reference. Representative types of cigarettes possessing filter elements incorporating carbonaceous materials have been available as "Benson & Hedges Multifilter" by Philip Morris Inc., in the State of Florida during 2005 as a Philip Morris Inc. test market brand known as "Marlboro Ultra Smooth," and as "Mild Seven" by Japan Tobacco Inc.

The carbonaceous material can be incorporated within a filter element by incorporating that carbonaceous material within paper or other sheet-like material (e.g., as a longitudinally disposed segment of gathered, shredded, or otherwise configured paper-like material). Alternatively, the carbonaceous material can be incorporated within a cavity (e.g., as products or granules within the central cavity region of a three-segment or stage filter element). Alternatively, the carbonaceous material can be dispersed within a fibrous filter material (e.g., as products or granules dispersed throughout a filter tow or gathered non-woven web material) as a segment of a longitudinally multi-segmented filter element (e.g., a two-segment filter element).

If desired, suitable catalytic compounds, e.g., for the conversion of carbon monoxide to carbon dioxide, can be incorporated into one or more segments of the filter element. Exemplary catalysts include noble metals (e.g., silver, gold, platinum), metal oxides, ceramics, and mixtures thereof.

Filter element components or segments for filter elements for multi-segment filtered cigarettes typically are provided from filter rods that are produced using traditional types of rod-forming units, such as those available as KDF-2 and KDF-3E from Hauni-Werke Korber & Co. KG. Typically, filter material, such as filter tow, is provided using a tow processing unit. An exemplary tow processing unit has been commercially available as E-60 supplied by Arjay Equipment Corp., Winston-Salem, N.C. Other exemplary tow processing units have been commercially available as AF-2, AF-3, and AF-4 from Hauni-Werke Korber & Co. KG. In addition, representative manners and methods for operating a filter material supply units and filter-making units are set forth in U.S. Pat. No. 4,281,671 to Byrne; U.S. Pat. No. 4,862,905 to Green, Jr. et al.; U.S. Pat. No. 5,060,664 to Siems et al.; U.S. Pat. No. 5,387,285 to Rivers; and U.S. Pat. No. 7,074,170 to Lanier, Jr. et al. Other types of technologies for supplying filter materials to a filter rod-forming unit are set forth in U.S. Pat. No. 4,807,809 to Pryor et al. and U.S. Pat. No. 5,025,814 to Raker; which are incorporated herein by reference.

Filter rods can be used to provide multi-segment filter rods. Such multi-segment filter rods then can be employed for the production of filtered cigarettes possessing multi-segment filter elements. An example of a two-segment filter element is a filter element possessing a first cylindrical segment incorporating activated charcoal products dispersed within or throughout cellulose acetate tow (e.g., a "dalmation" type of filter segment) at one end, and a second cylindrical segment that is produced from a filter rod produced essentially of plasticized cellulose acetate tow filter material at the other end. Filter elements also can have the form of so-called "patch filters" and possess segments incorporating carbonaceous materials and rupturable micro-encapsulated materials. The production of multi-segment filter rods can be carried out using the types of rod-forming units that traditionally have been employed to provide multi-segment cigarette filter components. Multi-segment cigarette filter rods can be manufactured using a cigarette filter rod making device available under the brand name Mulfi from Hauni-Werke Korber & Co. KG of Hamburg, Germany. Representative types of filter designs and components, including representative types of segmented cigarette filters, are set forth in U.S. Pat. No. 4,920,990 to Lawrence et al.; U.S. Pat. No. 5,012,829 to Thesing et al.; U.S. Pat. No. 5,025,814 to Raker; U.S. Pat. No. 5,074,320 to Jones et al.; U.S. Pat. No. 5,105,838 to White et al.; U.S. Pat. No. 5,271,419 to Arzonico et al.; U.S. Pat. No. 5,360,023 to Blakley et al.; U.S. Pat. No. 5,396,909 to Gentry et al.; and U.S. Pat. No. 5,718,250 to Banerjee et al.; U.S. Patent Appl. Pub. Nos. 2002/0166563 to Jupe et al.; 2004/0261807 to Dube et al.; 2005/0066981 to Crooks et al.; 2006/0090769 to Woodson; 2006/0124142 to Zhang et al.; 2006/0144412 to Mishra et al., and 2006/0157070 to Belcastro et al.; PCT Publication Nos. WO 03/009711 to Kim; and WO 03/047836 to Xue et al.; and U.S. patent application Ser. No. 11/226,932, filed Sep. 14, 2005, to Coleman III, et al.; which are incorporated herein by reference.

Multi-segment filter elements typically are provided from so-called "six-up" filter rods, "four-up" filter rods and "two-up" filter rods that are of the general format and configuration conventionally used for the manufacture of filtered cigarettes can be handled using conventional-type or suitably modified cigarette rod handling devices, such as tipping devices available as Lab MAX, MAX, MAX S, or MAX 80 from Hauni-Werke Korber & Co. KG. See, for example, the types of devices set forth in U.S. Pat. No. 3,308,600 to Erdmann et al.; U.S. Pat. No. 4,281,670 to Heitmann et al.; U.S. Pat. No. 4,280,187 to Reuland et al.; U.S. Pat. No. 4,850,301 to Greene, Jr. et al.; and U.S. Pat. No. 6,229,115 to Vos et al.; and U.S. Patent Application Publication Nos. 2005/0103355 to Holmes, 2005/1094014 to Read, Jr., and 2006/0169295 to Draghetti, each of which is incorporated herein by reference.

The type of flue-cured tobacco used in smoking products of the present technology can vary. Descriptions of flue-cured tobaccos, growing practices, harvesting practices and curing practices are set forth in Hawks, *Principles of Flue-Cured Tobacco Production* (1978), Sumner et al., *Guidelines for Temperature, Humidity, and Airflow Control in Tobacco Curing*, Univ. Georgia Res. Bull. 299 (1983), Todd, *Flue-*

*Cured Tobacco Producing a Healthy Crop* (1981), *Tobacco Production, Chemistry and Technology*, Davis et al. (Eds.) (1999), *Flue-Cured Tobacco Information*, NC Coop. Ext. Serv. (2002), and US Patent App. Pub. 2001/0000386 to Peele. Flue-cured tobaccos are also referred to as Virginia, bright or blond tobaccos. Representative flue-cured tobaccos include Coker 48, Coker 176, Coker 371-Gold, Coker 319, Coker 347, GL 939, K 149, K 326, K 340, K 346, K 358, K 394, K 399, K 730, NC 27NF, NC 37NF, NC 55, NC 60, NC 71, NC 72, NC 82, NC 95, NC 297, NC 606, NC 729, NC 2326, McNair 373, McNair 944, Ox 207, Ox414 NF, Reams 126, Reams 713, Reams 744, RG 8, RG 11, RG 13, RG 17, RG 22, RG 81, RG H4, RG H51, Speight H-20, Speight G-28, Speight G-58, Speight G-70, Speight G-108, Speight G-111, Speight G-117, Speight 168, Speight 179, Speight NF-3, Va 116 and Va 182. Preferred flue-cured tobaccos are those that are cured using the types of techniques and conditions set forth in US Patent App. Pub. 2001/0000386 to Peele. Preferred flue-cured tobaccos are aged for at least one year after curing is complete.

The type of burley tobacco utilized in smoking products of the present technology can vary. Descriptions of burley tobaccos, growing practices, harvesting practices and curing practices are set forth in Wiernik et al., *Rec. Adv. Tob. Sci.*, Vol. 21. p. 39-80 (1995), *Tobacco Production, Chemistry and Technology*, Davis et al. (Eds.) (1999) and *Burley Tobacco Information*, NC Coop. Ext. Serv. (2002). Representative burley tobaccos include Clay 402, Clay 403, Clay 502, Ky 14, Ky 907, Ky 910, Ky 8959, NC 2, NC 3, NC 4, NC 5, NC 2000, Tn 86, Tn 90, Tn 97, R 610, R 630, R 711, R 712, NCBH 129, Bu 21xKy 10, HB04P, Ky 14xL 8, Kt 200, Newton 98, Pedigo 561, Pf561 and Va509. Preferred burley tobaccos are air cured. Preferred air cured burley tobaccos are aged for at least one year after curing is complete.

Oriental tobacco used in smoking products of the present technology can also vary. Descriptions of Oriental-type tobaccos, growing practices, harvesting practices and curing practices are set forth in Wolf. *Aromatic or Oriental Tobaccos* (1962), Akehurst, *Tobacco* (1968), *Tobacco Encyclopedia*, Voges (Ed.) (1984), *Tobacco Production, Chemistry and Technology*, Davis et al. (Eds.) (1999). Oriental-type tobaccos also are referred to as Greek, aromatic, and Turkish tobaccos. Representative Oriental-type tobaccos include the Izmir, Basma, Mavra, and Samsun varieties. Other representative Oriental-type tobaccos include Trabzon, Thesalian, Tasova, Sinop, Tzmit, Hendek, Edirne, Semdinli, Adiyanman, Yayladag, Iskenderun, Duzce, Macedonian, Katerini, Prilep, Krumovgrad, Bafra, Bursa, Bucak, Bitlis and Balikesir tobaccos, as well as the so-called semi-Oriental tobaccos such as Sebinkarahisar, Borgka, and East Balkan tobaccos. Although Oriental-type tobaccos can be grown in a variety of locations throughout the world, typical Oriental tobaccos are grown in eastern Mediterranean regions such as Turkey, Greece, Bulgaria, Macedonia, Syria, Lebanon, Italy, Yugoslavia, and Romania. Preferred Oriental tobaccos are sun-cured. Preferred sun cured Oriental tobaccos are aged for at least one year after curing is complete.

The type of Maryland tobacco used in smoking products of the present technology can vary. Descriptions of Maryland tobaccos, growing practices, harvesting practices and curing practices are set forth in Tobacco Encyclopedia, Voges (Ed.) (1984), Aycock et al., Maryland Coop. Ext. (1984), Aycock et al., Maryland Coop. Ext. (1995), and *Tobacco Production, Chemistry and Technology*, Davis et al. (Eds.) (1999). Representative Maryland tobaccos include Md 10, Md 40, Md 201, Md 609, Md 872, and Md 341. Preferred Maryland tobaccos are air cured. and often are referred to as light air cured tobaccos. Preferred air cured Maryland tobaccos are aged for at least one year after curing is complete.

In some embodiments, the tobacco materials and/or deflavored rosemary or heat-treated rosemary may be treated and/or incorporate tobacco additives of the type that are traditionally used for the manufacture of cigarette, such as casing and/or top dressing components. See, for example, U.S. Pat. No. 3,419,015 to Wochnowski; U.S. Pat. No. 4,054,145 to Berndt et al.; U.S. Pat. No. 4,887,619 to Burcham. Jr. et al.; U.S. Pat. No. 5,022,416 to Watson; U.S. Pat. No. 5,103,842 to Strang et al.; and U.S. Pat. No. 5,711,320 to Martin. Typical casing materials include water, sugars, and syrups (e.g., sucrose, glucose, and high fructose corn syrup), humectants (e.g., glycerin or propylene glycol), flavoring agents (e.g., cocoa and licorice), and $C_3$-$C_{20}$ organic acids such as levulinic acid, pynivic acid, and acetic acid. Added components may also include top dressing materials (e.g., flavoring materials such as menthol). See, for example, U.S. Pat. No. 4,449,541 to Mays et al. Additives also can be added to the tobacco and/or deflavored rosemary or heat-treated rosemary using the types of equipment described in U.S. Pat. No. 4,995,405 to Lettau, or equipment available as Menthol Application System (MAS) from Kohl Maschinenbau GmbH. The selection of particular casing and top dressing components is dependent upon factors such as the sensory characteristics that are desired, and the selection and use of those components will be readily apparent to those skilled in the art of cigarette design and manufacture. See, Gutcho, Tobacco Flavoring Substances and Methods, Noyes Data Corp. (1972) and Leffingwell et al., Tobacco Flavoring for Smoking Products (1972).

In some embodiments, the tobacco materials may have been treated or may have one or more additives incorporated for proposes of altering the overall character or nature of the tobacco materials utilized in tobacco products. For example, a heat treatment process can be used to impart a desired color or visual character to the tobacco material, desired sensory properties to the tobacco material, or a desired physical nature or texture to the tobacco material. See U.S. Pat. No. 8,434,496 to Chen et al., which is incorporated herein by reference.

In some embodiments, the sensory attributes of cigarette smoke can be enhanced by incorporating flavoring materials into various components of a cigarette. See, Leffingwell et al., Tobacco Flavoring for Smoking Products, R.J. Reynolds Tobacco Company (1972). Exemplary flavoring additives include menthol and products of Maillard reactions, such as pyrazines, aminosugars, and Amadori compounds. Various processes for preparing flavorful and aromatic compositions for use in tobacco compositions are set forth in U.S. Pat. No. 3,424,171 to Rooker; U.S. Pat. No. 3,476,118 to Luttich; U.S. Pat. No. 4,150,677 to Osborne, Jr. et al.; U.S. Pat. No. 4,986,286 to Roberts et al.; U.S. Pat. No. 5,074,319 to White et al.; U.S. Pat. No. 5,099,862 to White et al.; U.S. Pat. No. 5,235,992 to Sensabaugh, Jr.; U.S. Pat. No. 6,298,858 to Coleman, III et al.; U.S. Pat. No. 6,325,860 to Coleman, III et al.; U.S. Pat. No. 6,428,624 to Coleman, III et al.; U.S. Pat. No. 6,440,223 to Dube et al.; U.S. Pat. No. 6,499,489 to Coleman, III; and U.S. Pat. No. 6,591,841 to White et al.; US Patent Appl. Publication No. 2004/0173228 to Coleman, III; and U.S. application Ser. No. 12/191,751 to Coleman, III et al., each of which is incorporated herein by reference. Such processes often include the application of heat to a tobacco material, which can result in reactions that form certain byproducts.

In some embodiments, the smoking products described herein may include botanical material(s) in addition to rosemary. As used herein, "botanical material(s)" refers to any plant material, including plant material in its natural form and plant material derived from natural plant materials, such as extracts or isolates from plant materials or treated plant materials (e.g., plant materials subjected to heat treatment, fermentation, or other treatment processes capable of altering the chemical nature of the material). For the purposes of the present disclosure, "botanical material(s)" includes but is not limited to "herbal materials," which refer to seed-producing plants that do not develop persistent woody tissue and are often valued for their medicinal or sensory characteristics (e.g., teas or tisanes). Reference to botanical material(s) is not intended to include tobacco materials (i.e., does not include any *Nicotiana* species). The other botanical material(s) used in the present technology may comprise, without limitation, any of the compounds and sources set forth herein, including mixtures thereof. Certain botanical materials of this type are sometimes referred to as dietary supplements, nutraceuticals, "phytochemicals" or "functional foods." In some embodiments, the botanical material(s) may be included to enhance or incorporate a flavor into the smoking product. In some embodiments, the botanical material(s) may contribute to a reduction in mouth and/or throat irritation otherwise associated with the smoking product.

Exemplary botanical material(s), many of which are associated with antioxidant characteristics, include without limitation acai berry, alfalfa, allspice, annatto seed, apricot oil, basil, bee balm, wild bergamot, black pepper, blueberries, borage seed oil, bugleweed, cacao, calamus root, catnip, catuaba, cayenne pepper, chaga mushroom, chervil, cinnamon, dark chocolate, potato peel, grape seed, *ginseng*, gingko *biloba*, Saint John's Wort, saw palmetto, green tea, black tea, black cohosh, cayenne, chamomile, cloves, cocoa powder, cranberry, dandelion, grapefruit, honeybush, *echinacea*, garlic, evening primrose, feverfew, ginger, goldenseal, hawthorn, hibiscus flower, jiaogulan, kava, lavender, licorice, marjoram, milk thistle, mints (menthe), oolong tea, beet root, orange, oregano, *papaya*, pennyroyal, peppermint, red clover, rooibos (red or green), rosehip, sage, clary sage, savory, spearmint, *spirulina*, slippery elm bark, sorghum bran hi-tannin, sorghum grain hi-tannin, sumac bran, comfrey leaf and root, goji berries, gutu kola, thyme, turmeric, uva *ursi*, valerian, wild yam root, wintergreen, yacon root, yellow dock, yerba mate, yerba santa, bacopa monniera, withania somnifera, and *silybum marianum*.

Generally, botanical material(s) often include compounds from various classes known to provide certain bioactive effects, such as minerals, vitamins such a ascorbic acid, isoflavones, phytoesterols, allyl sulfides, dithiolthiones, isothiocyanates, indoles, lignans, flavonoids, polyphenols, plant phenolics, tocopherols, ubiquinone, benzodioxoles, carotenoids, etc. More specifically, typical antioxidants from botanicals can be classified in the following groups: monoterpenoid phenols; alcohols such as thymol, carvacol, menthol; p-cymene; diterpene phenols such as carnosic acid, carnosol, rosmanol; hydroxycinnamic type compounds such as caffeic acid, chlorogenic acid, rosmarinic acid, p-coumaric acid, resveratrol, curcumin, eugenol, cinnamaladehyde; hydroxybenzoic acids and derivatives such as gallic acid, protocatechuic acid, propyl gallate; 2-benzopryrones such as scopoletin, coumarin; 4-benzopyrones such as quercetin, genistein, naringenin, diosmin, rutin; dihydrochalcones such as aspalathin, notophagin; flavanols such as epicatechin, epigallocatechin, epicatechin gallate, epigallo- catechin gallate; anthocyanins and anthocyanidins; triterpenes such as ursolic acid, oleanolic acid, betulinic acid, betulonic acid; tocopherols such as α, β, γ, δ-tocopherols; tocotrienols; carotenoids such as β-carotene or lutein; ubiquinone, CoQ10; ascorbyl palmitate; benzodioxoles such as myristicin, piperine, safrole; and other compounds such as gambogic acid, gingerol, and the like. Beyond antioxidant properties, certain compounds noted above can also have properties such as distinctive flavor, color, antiseptic properties, anti-carcinogenic effects, etc.

Exemplary compounds found in botanical materials include, but are not limited to, propylene glycol, lactic acid, glycolic acid, alanine, camphor, pyruvic acid, aspalathin, borneol, menthol, phosphate, glycerin, proline, succinic acid, thymol, glyceric acid, 2-butenedioic acid, 3-hydroxyglutaric acid, malic acid, 5-oxoproline (pyroglutamic acid), aspartic acid, trihydroxybutanoic acid, glutamine, asparagine, levoglucosan, xylitol, ribitol, 2-keto-L-gluconic acid, fructose, caffeine, citric acid, glucosamine, neophytadiene, altrose, quinic acid, xylulose, glucose, inositol, 2-amino-2-deoxyglucose, glucitol, ascorbic acid, glucose, gallic acid, gluconic acid, galactaric acid, hexadecanoic acid, 3,4-dihydroxyphenyl-2-hydroxypropionic acid, glucuronic acid, myoinositol, caffeic acid, tryptophan, linolenic acid, octadecanoic acid, galacturonic acid, rosmaricin, carnosic acid, melibiose, carnosol, phitosterol, sucrose, rosmanol, 2,5-deoxyfructosazine, 2,6-deoxyfructosazine, fructosazine, maltitol, epicatechin, nothofagin, orientin, catechin, epigallocatechin, coumaroyl quinic acid, tocoferol, chloro genic acid, stigmasterol, rosmarinic acid, betulinic acid, oleanolic acid, ursolic acid, glyderinine, epicatechin gallate, catechin gallate, epigallocatechin gallate, gallocatechin gallate, solanesol, and the like. For additional exemplary compounds, see, e.g., Santhosh et al., Phytomedicine, 12 (2005) 216-220, which is incorporated herein by reference.

As noted above, the tobacco material can include non-tobacco filler materials, and such materials preferably have general physical characteristics (e.g., size, shape, weight, density, and the like) that are similar to tobacco cut filler traditionally used for tobacco rod manufacture. The filler material may comprise paper, pulp, wood, plants, and mixtures thereof. The filler material may be woven or nonwoven, particulate, shredded, or granular.

Substantial listings of various types of tobacco substitute materials can be found in U.S. Pat. No. 4,079,742 to Rainer et al. and U.S. Pat. No. 4,771,795 to White et al. Certain cigarette-type products that employ non-tobacco materials (e.g., dried vegetable leaves, such as lettuce leaves) as filler that is burned to produce smoke that resembles tobacco smoke have been marketed under the trade names "CUBEBS," "TRIUMPH," "JAZZ," and "BRAVO." For example, such materials are described in U.S. Pat. No. 4,700,727 to Torigian. Furthermore, tobacco substitute materials having the trade names "CYTREL" and "NSM" were introduced in Europe during the 1970s. Representative types of proposed synthetic tobacco substitute materials, smokable materials incorporating tobacco and other components, and cigarettes incorporating those materials, are described in British Patent No. 1,431,045; and U.S. Pat. No. 3,738,374 to Bennett; U.S. Pat. No. 3,844,294 to Webster; U.S. Pat. No. 3,878,850 to Gibson et al.; U.S. Pat. No. 3,931,824 to Miano et al.; U.S. Pat. No. 3,943,941 to Boyd et al.; U.S. Pat. No. 4,044,777 to Boyd et al.; U.S. Pat. No. 4,233,993 to Miano et al.; U.S. Pat. No. 4,286,604 to Ehretsmann et al.; U.S. Pat. No. 4,326,544 to Hardwick et al.; U.S. Pat. No. 4,920,990 to Lawrence et al.; U.S. Pat. No. 5,046,514 to Bolt; U.S. Pat. No. 5,074,321 to Gentry et al.;

U.S. Pat. No. 5,092,353 to Montoya et al.; U.S. Pat. No. 5,778,899 to Saito et al.; U.S. Pat. No. 6,397,852 to McAdam; and U.S. Pat. No. 6,408,856 to McAdam. Furthermore, various types of highly processed smokable materials incorporating tobacco and other ingredients are set forth in U.S. Pat. No. 4,823,817 to Luke; U.S. Pat. No. 4,874,000 to Tamol et al.; U.S. Pat. No. 4,977,908 to Luke; U.S. Pat. No. 5,072,744 to Luke et al.; U.S. Pat. No. 5,829,453 to White et al.; and U.S. Pat. No. 6,182,670 to White et al.

In some embodiments, tobacco rods (i.e., cigarette rods) are manufactured using a cigarette making machine, such as a conventional automated cigarette rod making machine. Exemplary cigarette rod making machines are of the type commercially available from Molins PLC or Hauni-Werke Korber & Co. KG. For example, cigarette rod making machines of the type known as MkX (commercially available from Molins PLC) or PROTOS (commercially available from Hauni-Werke Korber & Co. KG) can be employed. A description of a PROTOS cigarette making machine is provided in U.S. Pat. No. 4,474,190 to Brand, at col. 5, line 48 through col. 8, line 3, which is incorporated herein by reference. Types of equipment suitable for the manufacture of cigarettes also are set forth in U.S. Pat. No. 4,781,203 to La Hue; U.S. Pat. No. 4,844,100 to Holznagel; U.S. Pat. No. 5,131,416 to Gentry; U.S. Pat. No. 5,156,169 to Holmes et al.; U.S. Pat. No. 5,191,906 to Myracle, Jr. et al.; U.S. Pat. No. 6,647,870 to Blau et al.; U.S. Pat. No. 6,848,449 to Kitao et al.; and U.S. Pat. No. 6,904,917 to Kitao et al.; and U.S. Patent Application Publication Nos. 2003/0145866 to Hartman; 2004/0129281 to Hancock et al.; 2005/0039764 to Barnes et al.; and 2005/0076929 to Fitzgerald et al.; each of which is incorporated herein by reference.

The components and operation of conventional automated cigarette making machines will be readily apparent to those skilled in the art of cigarette making machinery design and operation. For example, descriptions of the components and operation of several types of chimneys, tobacco filler supply equipment, suction conveyor systems and garniture systems are set forth in U.S. Pat. No. 3,288,147 to Molins et al.; U.S. Pat. No. 3,915,176 to Heitmann et al.; U.S. Pat. No. 4,291,713 to Frank; U.S. Pat. No. 4,574,816 to Rudszinat; U.S. Pat. No. 4,736,754 to Heitmann et al.; U.S. Pat. No. 4,878,506 to Pinck et al.; U.S. Pat. No. 5,060,665 to Heitmann; U.S. Pat. No. 5,012,823 to Keritsis et al.; and U.S. Pat. No. 6,360,751 to Fagg et al.; and U.S. Patent Publication No. 2003/0136419 to Muller; each of which is incorporated herein by reference. The automated cigarette making machines of the type set forth herein provide a formed continuous cigarette rod or smokable rod that can be subdivided into formed smokable rods of desired lengths.

Various types of cigarette components, including tobacco types, tobacco blends, top dressing and casing materials, blend packing densities and types of paper wrapping materials for tobacco rods, can be employed. See, for example, the various representative types of cigarette components, as well as the various cigarette designs, formats, configurations and characteristics, that are set forth in Johnson, Development of Cigarette Components to Meet Industry Needs, 52$^{nd}$ T.S.R.C. (September, 1998); U.S. Pat. No. 5,101,839 to Jakob et al.; U.S. Pat. No. 5,159,944 to Arzonico et al.; U.S. Pat. No. 5,220,930 to Gentry and U.S. Pat. No. 6,779,530 to Kraker; U.S. Patent Publication Nos. 2005/0016556 to Ashcraft et al.; 2005/0066986 to Nestor et al.; and 2005/0076929 to Fitzgerald et al.; and U.S. patent application Ser. No. 11/226,932, filed Sep. 14, 2005, to Coleman, III et al.; Ser. No. 11/375,700, filed Mar. 14, 2006, to Thomas et al. and Ser. No. 11/408,625, filed Apr. 21, 2006, to Oglesby; each of which is incorporated herein by reference. In some embodiments, the entire cigarette rod is composed of smokable material (e.g., tobacco cut filler) and deflavored or heat-treated rosemary and a layer of circumscribing outer wrapping material.

As used herein, weight percent (i.e., wt %) in reference to the tobacco, deflavored rosemary, or heat-treated rosemary refers to the dry weight percent.

EXAMPLES

The following examples are intended to more specifically illustrate the present smoking products according to various embodiments described above. These examples should in no way be construed as limiting the scope of the present technology.

Example 1

The Detection of Analytes Before Heating Rosemary

Rosemary from various sources were analyzed as is (i.e., not heated) for their analyte levels using LC-MS/MS in MRM mode. The HPLC separation was performed on an Agilent 1200 HPLC binary system that consisted of a binary pump, an autosampler with cooling capability, and a column thermostatted compartment. The HPLC chromatographic separation was achieved on two connected Gemini 5u C18 columns, 150×4.6 mm, with 5 μm particles from Phenomenex (Torrance, Calif., USA). The MS/MS system was an API-6500 triple quadrupole mass spectrometer (AB Sciex, Framingham, Mass., USA), controlled using Analyst 1.6.2 software, and the peak integration was performed with MultiQuant 3.0.1 software. From each sample, 100 mg of finely ground rosemary (weighed with 0.1 mg precision) was extracted for 30 min with 4 mL methanol on a wrist action shaker. A portion of the solution was then filtered through a 0.45 μm polyvinilidene fluoride (PVDF) filter. From this solution, 100 μL were placed in a 2 mL screw top cap vial. To the vial were added 200 μL of a solution of internal standard. The internal standard solution contained 386 μg/mL cholic acid in methanol. The volume for the analyzed solution was brought to 1 mL by adding 700 μL methanol. The quantitation of the acids was performed by LC-MS/MS based on their peak area ratio by the peak area of the internal standard. The characteristics for the MS/MS detection for the acid analytes rosmarinic, carnosic, betulinic, oleanolic, ursolic, and betul-18-en-oic acid and the internal standard are listed in Table 1. Samples were similarly prepared for the analysis of 1,8-cineole, camphor, and borneol, however, no internal standard was added to the solution for these three analytes.

TABLE 1

Parameters for the MS/MS detection in MRM negative ionization mode.

| Compound | Ion for Q1 | Ion for Q3 | Time (ms) | DP$^1$ (V) | EP$^2$ (V) | CE$^3$ (V) |
|---|---|---|---|---|---|---|
| Rosmarinic acid | 359.1 | 161.1 | 100 | −35 | −5 | −20 |
| Carnosic acid | 331.2 | 287.2 | 100 | −35 | −5 | −35 |
| Betulinic acid | 455.4 | 455.4 | 100 | −200 | −3 | −25 |
| Oleanolic acid | 455.4 | 455.4 | 100 | −200 | −3 | −25 |

TABLE 1-continued

Parameters for the MS/MS detection in MRM negative ionization mode.

| Compound | Ion for Q1 | Ion for Q3 | Time (ms) | $DP^1$ (V) | $EP^2$ (V) | $CE^3$ (V) |
|---|---|---|---|---|---|---|
| Ursolic acid | 455.4 | 455.4 | 100 | −200 | −3 | −25 |
| Betul-18-en-oic acid | 453.4 | 453.4 | 100 | −200 | −3 | −25 |
| I.S. Cholic acid | 407.4 | 407.4 | 100 | −35 | −5 | −35 |

[1]DP = declustering potential
[2]EP = entrance potential
[3]CE = collision energy For the quantitation by the LC-MS/MS, calibration curves were generated for rosmarinic, carnosic, oleanolic, ursolic, and betulinic acids as well as 1,8-cineole, camphor, and borneol. The calibrations for the acids were done using eight standard levels (between 1.94 to 77.6 μm/mL for rosmarinic acid, 2.5 to 100 μm/mL for carnosic acid, 1.136 to 90.88 μm/mL for betulinic acid, 1.00 to 80.00 μm/mL for oleanolic acid, and 1.054 to 84.32 μm/mL for ursolic acid). Each standard solution contained the same amount of 77.6 μm/mL cholic acid used as the internal standard. The equations for calibration were linear for all the acids except rosmarinic. The equations of the form $Y=a X^2+b X+c$ for the calibration curves and the $R^2$ values for the trend line are given in Table 2A. In Table 2A, X=(peak area of standard)/(peak area of internal standard) and Y is μg/mL analyte. Because betul-18-enoic acid (i.e., (3β)-3-hydroxy-lupa-18,20(29)-dien-28-oic) is not commercially available, its quantitation was performed using the equation for betulinic acid.

TABLE 2A

Equations for the calibration of the acid analytes

| Analyte | Type | a | b | c | $R^2$ |
|---|---|---|---|---|---|
| Rosmarinic acid | quadratic | −1.102e3 | 5.896e2 | 5.729e−1 | 0.9985 |
| Carnosic acid | linear | 0 | 7.847 | 1.964 | 0.9862 |
| Betulinic acid | linear | 0 | 11.767 | −1.291 | 0.9991 |
| Oleanolic acid | linear | 0 | 18.112 | −1.697 | 0.9987 |
| Ursolic acid | linear | 0 | 18.138 | −2.284 | 0.9985 |

The calibrations for 1,8-cineole, camphor, and borneol were similarly preformed using nine standard levels between 4.1 to 1062.0 μg/mL for 1,8-cineole, 1.8 to 325.0 μg/mL for camphor, and 1.1 to 299.0 μg/mL for borneol. No internal standard was used in the quantitation. The equations for calibration were quadratic for all the analytes. The equations were of the form $Y=a X^2+b X$ (all passing through origin), where X is peak area of standard and Y is μg/mL analyte. The calibration equations are given in Table 2B, together with the $R^2$ values.

TABLE 2B

Equations for the calibration of the analytes 1,8-cineole, camphor, and borneol

| Analyte | Type | a | b | $R^2$ |
|---|---|---|---|---|
| 1,8-Cineole | quadratic | 1.6262e−13 | 1.2088e−5 | 0.9984 |
| Camphor | quadratic | −4.0112e−14 | 7.9887e−6 | 0.9971 |
| Borneol | quadratic | 8.8271e−15 | 1.7207e−6 | 0.9688 |

Table 3 presents the sources of the various rosemary samples.

TABLE 3

Sources of rosemary samples.

| Spl. No. | Sample description | Sample source |
|---|---|---|
| Ros 0 | Organic leaf | Starwest Botanicals Inc. (Sacramento, CA, USA) |
| Ros. 1 | Original leaf | Whole Foods Market (Braselton, GA, USA) |
| Ros. 2 | Control Leaf | Whole Foods Market (Braselton, GA, USA) |
| Ros. 3 | El Club Mexicano | El Club Mexicano (Asheboro, NC, USA) |
| Ros. 4 | Ground Fresh Market | Fresh Market (Greensboro, NC, USA) |
| Ros. 5 | Leaf Fresh Market | Fresh Market (Greensboro, NC, USA) |
| Ros. 6 | Leaf Frontier A | A&S Natural Health, (Winston-Salem, NC, USA) |
| Ros. 7 | Leaf Frontier B | Frontiere Natural Product Co-op, (Norway, IA, USA) |

Table 4A presents the levels of betul-en-ic acid (i.e., betul-18-enoic acid), betulinic acid, carnosic acid, oleanolic acid, rosmarinic acid, and ursolic acid expressed in mg/g plant material with about 9.5% moisture (not corrected for moisture). All measurements were performed in triplicates, and the RSD % for the results were all below 5%, except for the measurements of rosmarinic acid with RSD %=6.8%. The table also indicates the average values across the samples, maximum difference between the samples, and RSD % between the samples. It was determined that the rosemary contained relatively high levels of betulinic, oleanolic, betul-18-en-oic, and ursolic acids (in the range of 10 to 25 mg/g dry plant material for each acid).

TABLE 4A

Levels of the acids in rosemary samples 0-7.

| Spl. No. | Betul-en-ic | Betu-linic | Carnosic | Olea-nolic | Rosmarinic | Ur-solic |
|---|---|---|---|---|---|---|
| Ros 0 | 9.77 | 12.61 | 24.48 | 13.23 | 16.61 | 23.29 |
| Ros 1 | 10.72 | 13.19 | 30.47 | 13.78 | 16.25 | 24.39 |
| Ros 2 | 9.89 | 13.85 | 25.75 | 14.53 | 13.04 | 26.18 |
| Ros 3 | 9.71 | 13.32 | 24.75 | 13.91 | 13.43 | 25.05 |
| Ros 4 | 10.38 | 12.68 | 17.30 | 14.89 | 12.58 | 27.30 |
| Ros 5 | 8.71 | 14.30 | 23.23 | 13.94 | 13.14 | 25.50 |
| Ros 6 | 13.50 | 15.14 | 22.81 | 15.78 | 11.18 | 25.01 |
| Ros 7 | 11.46 | 15.58 | 20.22 | 15.27 | 18.40 | 26.24 |
| Average | 10.52 | 13.83 | 23.63 | 14.42 | 4.34 | 25.37 |
| RSD % | 13.79% | 7.96% | 16.45% | 5.93% | 17.16% | 4.87% |
| Max. diff. mg/g | 4.79 | 2.97 | 13.17 | 2.55 | 7.22 | 4.01 |

Table 4B presents the levels of 1,8-cineole, camphor, and borneol expressed in mg/g plant material with about 9.5% moisture (not corrected for moisture). Relatively large variations in the level of the compounds were seen between the rosemary samples. This indicates that the flavor of rosemary can differ from the plant material obtained from one commercial source to another.

TABLE 4B

Levels of 1,8-cineole, camphor, and borneol in rosemary samples 0-7.

| Spl. No. | 1,8-Cineole | Camphor | Borneol |
|---|---|---|---|
| Ros 0 | 6.77 | 2.76 | 0.38 |
| Ros 1 | 8.23 | 2.71 | 0.41 |
| Ros 2 | 5.47 | 3.72 | 0.47 |

TABLE 4B-continued

Levels of 1,8-cineole, camphor, and borneol in rosemary samples 0-7.

| Spl. No. | 1,8-Cineole | Camphor | Borneol |
|---|---|---|---|
| Ros 3 | 11.16 | 5.70 | 0.66 |
| Ros 4 | 1.08 | 1.85 | 0.34 |
| Ros 5 | 7.84 | 4.79 | 0.55 |
| Ros 6 | 1.97 | 2.83 | 0.46 |
| Ros 7 | 4.58 | 3.69 | 0.55 |
| Max. diff. mg/g | 10.08 | 3.85 | 0.32 |

Example 2

The Detection of Analytes after Heating Rosemary

About 2 g of Ros 0 was heated in aluminum weighing dishes for various times and temperatures followed by analyzation of the sample for analyte levels using the same LC-MS/MS methods described above. The times and temperatures are shown in Table 5. Experiment 0 indicates the level of each analyte as measured in sample Ros 0, without being exposed to any heating but corrected for 10% moisture.

TABLE 5

Heating temperature and time duration of rosemary samples.

| Experiment | Temp ° C. | Time (hours) |
|---|---|---|
| 0 | ambient | (not applicable) |
| 1 | 100 | 1 |
| 2 | 100 | 2 |
| 3 | 100 | 4 |
| 4 | 150 | 1 |
| 5 | 150 | 2 |
| 6 | 150 | 4 |
| 7 | 200 | 1 |
| 8 | 200 | 2 |
| 9 | 200 | 4 |
| 10 | 250 | 1 |
| 11 | 250 | 2 |
| 12 | 250 | 4 |

The results of the variation in the level of each analyzed acid are shown in FIGS. 1-9, which indicate the level of acid in grams per 100 gram of rosemary.

FIG. 1 demonstrates that betul-8-en-oic acid in rosemary is not affected by heating at 100° C., suffers a slight decrease by heating at 150° C. (even for a duration of 4 hours), starts to decompose at 200° C. with the decomposition more significant at a longer duration of heating, and almost complete decomposes when heating takes place at 250° C.

Figure 2:
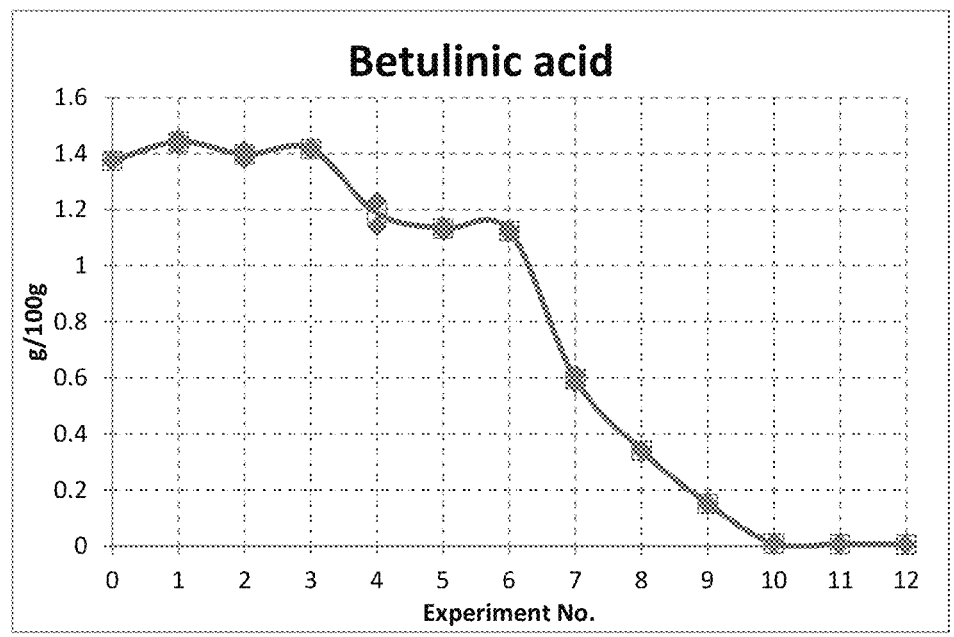
FIG. 2 illustrates the variation in the level of betulinic acid for different heating experiments (g acid/100 g rosemary), according to some embodiments.

FIG. 2 demonstrates that betulinic acid in rosemary behaves similarly to betul-8-en-oic acid during heating, with the difference that heating at 200° C. produces less decomposition. The compound is not affected by heating at 100° C., suffers a slight decrease by heating at 150° C., and is completely decomposed by heating at 250° C.

Figure 3:
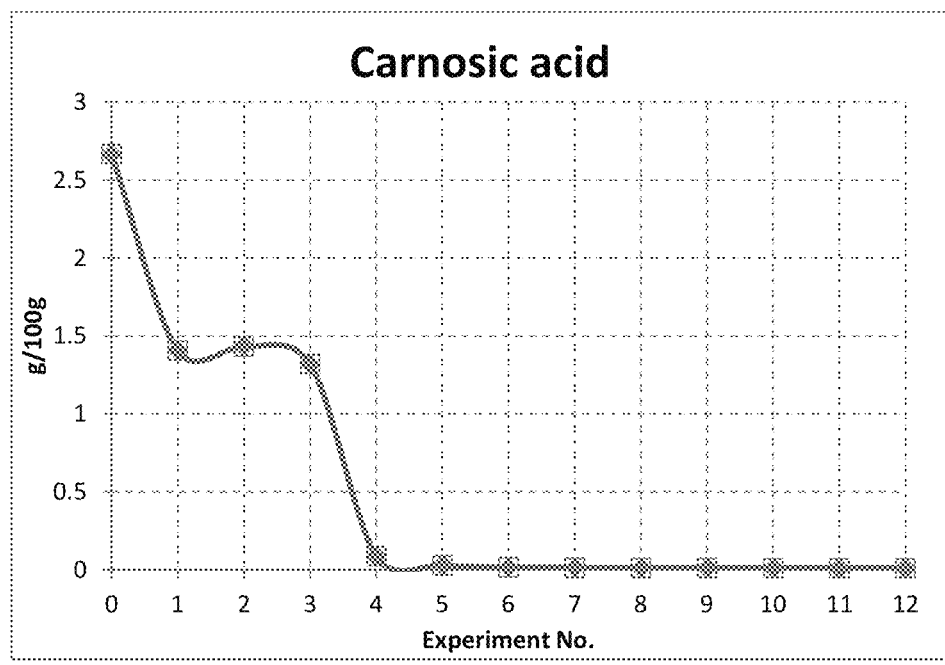
FIG. 3 illustrates the variation in the level of carnosic acid for different heating experiments (g acid/100 g rosemary), according to some embodiments.

FIG. 3 demonstrates that carnosic acid decomposes much easier than the pentacyclic triterpenoid acids. Even heating at 100° C. affects the level of this acid (reduction to about half of its initial level) and the heating of rosemary at 150° C. nearly leads to complete decomposition of carnosic acid.

Figure 4:
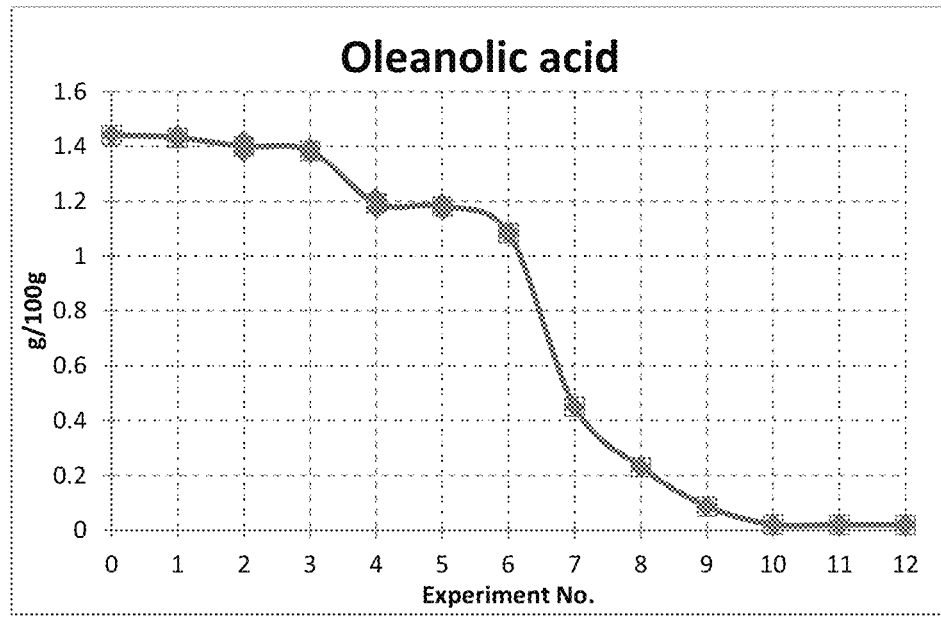
FIG. 4 illustrates the variation in the level of oleanolic acid for different heating experiments (g acid/100 g rosemary), according to some embodiments.

FIG. 4 demonstrates that oleanolic acid in rosemary behaves very similarly to betulinic acid during heating. The compound is not affected by heating at 100° C., suffers a slight decrease by heating at 150° C., starts decomposing by heating at 200° C. with more decomposition when exposed to this temperature for longer time, and is completely decomposed by heating at 250° C.

Figure 5:
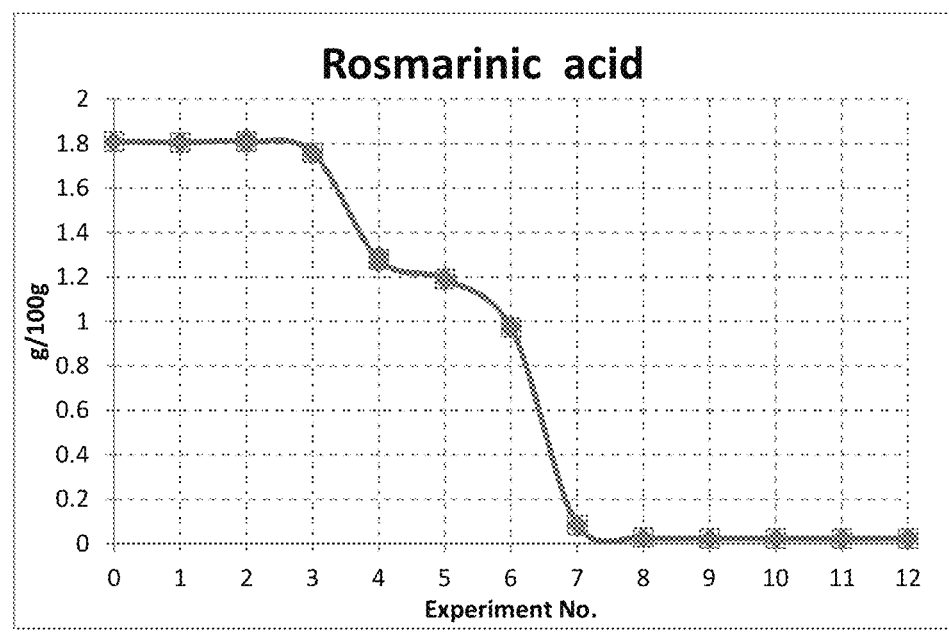
FIG. 5 illustrates the variation in the level of rosmarinic acid for different heating experiments (g acid/100 g rosemary), according to some embodiments.

FIG. 5 demonstrates that rosmarinic acid in rosemary is not affected by heating at 100° C., but starts decomposing at 150° C., with more decomposition at higher exposure time at this temperature. Rosmarinic acid in rosemary is nearly completely decomposed when heating takes place at 200° C. or 250° C.

Figure 6:
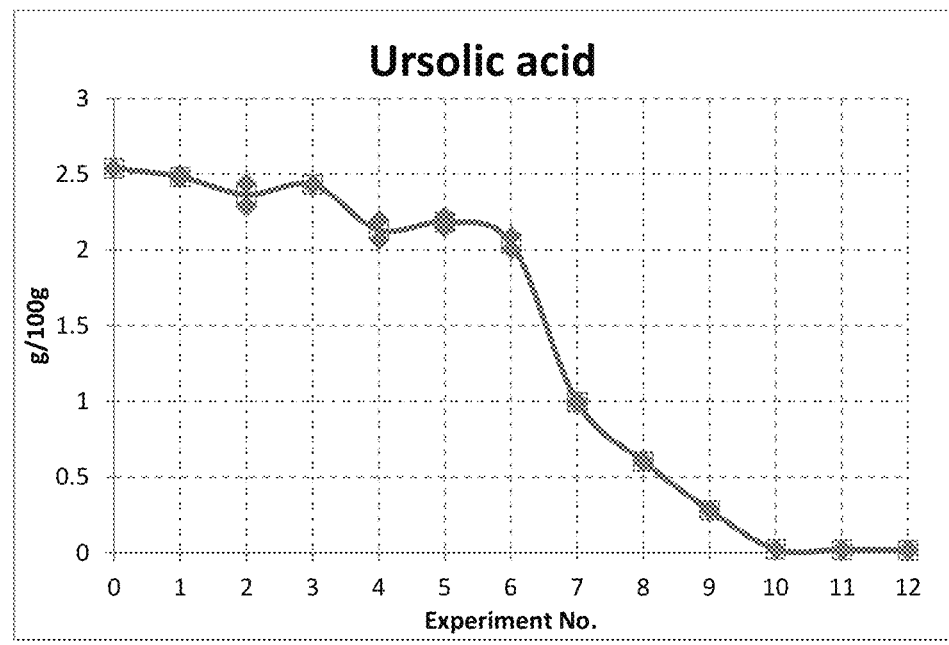
FIG. 6 illustrates the variation in the level of ursolic acid for different heating experiments (g acid/100 g rosemary), according to some embodiments.

FIG. 6 demonstrates that ursolic acid in rosemary is rather stable to heat. Heating of this acid at 150° C. affects the level only slightly. Heating at 200° C. starts a decomposition process similar to that seen in the other pentacyclic triterpenoid acids, and heating at 250° C. leads to decomposition.

Figure 7:
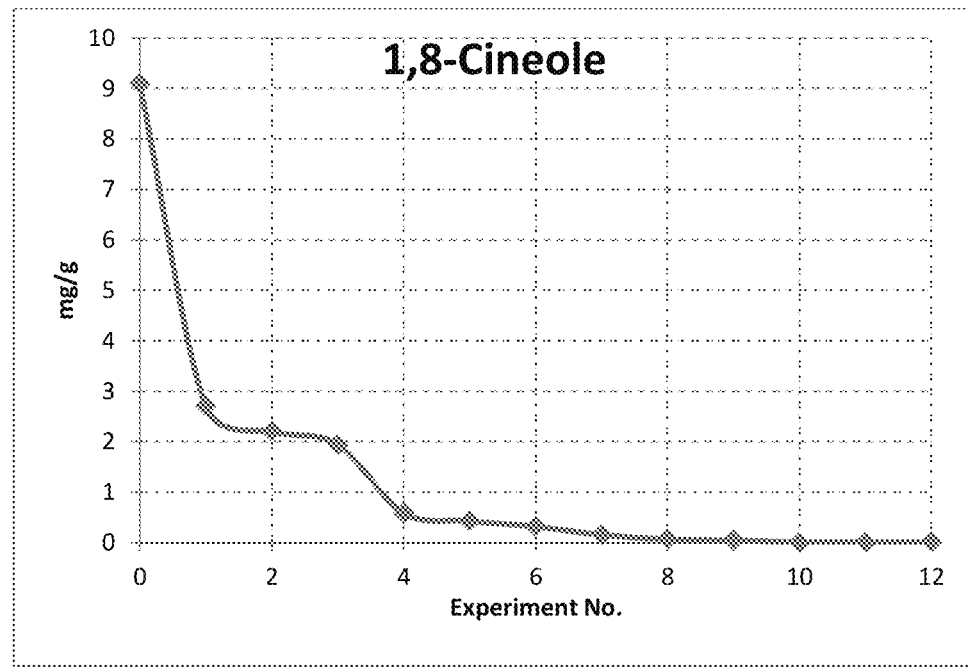
FIG. 7 illustrates the variation in the level of 1,8-cineole for different heating experiments (g acid/100 g rosemary), according to some embodiments.
Figure 8:
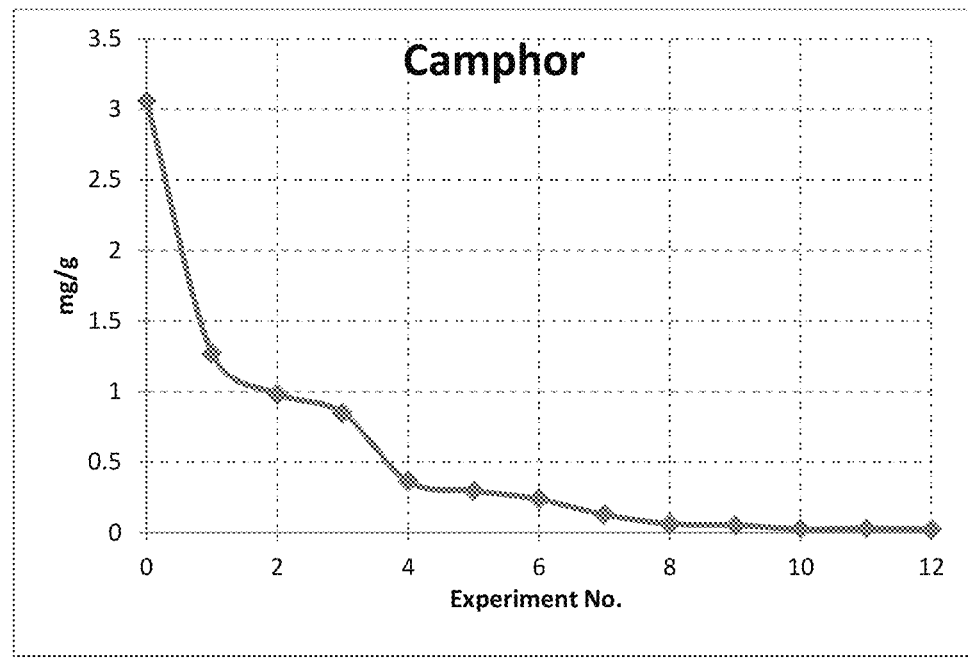
FIG. 8 illustrates the variation in the level of camphor for different heating experiments (g acid/100 g rosemary), according to some embodiments.
Figure 9:
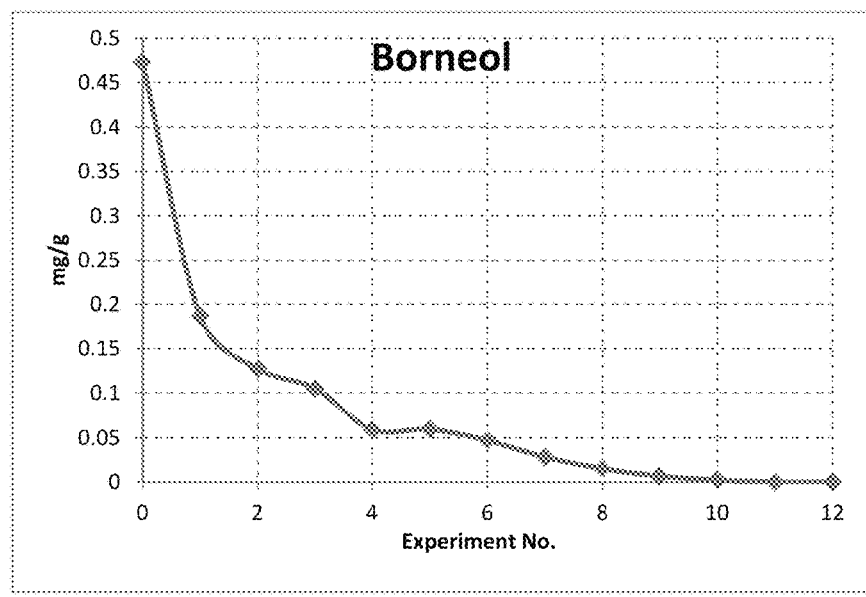
FIG. 9 illustrates the variation in the level of borneol for different heating experiments (g acid/100 g rosemary), according to some embodiments.

FIGS. 7-9 demonstrates that heating has a strong effect on decreasing the level of 1,8-cineole, camphor, and borneol in rosemary. The heating time, also affects the decrease, but to a lesser extent (when it is applied for more than one hour).

Example 3

Analytes in Smoke from Tobacco and Rosemary Cigarettes

Camel Blue Tobacco blend (approximately 95 wt %) was blended with rosemary that had been heated at about 150° C. for about 4 hours (approximately 5 wt % leaf dry with 9.5% moisture). The composition was formed into cigarettes. The cigarettes were conditioned and the smoke from the cigarettes was collected using a Cerulean SM 450 smoking machine (Cerulean, Linford Wood East, MK14 6LY, UK). The smoking was performed using 35 mL puff volume, 2 s puff, and 60 s puff interval, with the cigarette filters not having the ventilation blocked. Smoke from ten cigarettes was collected in each run on a 44-mm diameter Cambridge pad. Each Cambridge pad was extracted with 10 mL of methanol for 30 min on a wrist action shaker (Burrell Co., Pittsburgh, Pa., USA). From the methanol solution, 800 µL were placed in a 2 mL screw top cap vial and to the vial were added 200 µL of a solution of internal standard. This solution was analyzed by the LC-MS/MS procedure described above. Table 6 indicates the total particulate matter (TPM) weight from the samples.

TABLE 6

Total Particulate Matter

| Rep. No. | Weight pad before (g) | Weight pad after (g) | TPM (g)/ 10 cigs. |
|---|---|---|---|
| 1 | 42.8700 | 43.0047 | 0.1347 |
| 2 | 40.7193 | 40.8486 | 0.1293 |
| 3 | 42.0636 | 42.2006 | 0.1370 |

Figure 10:
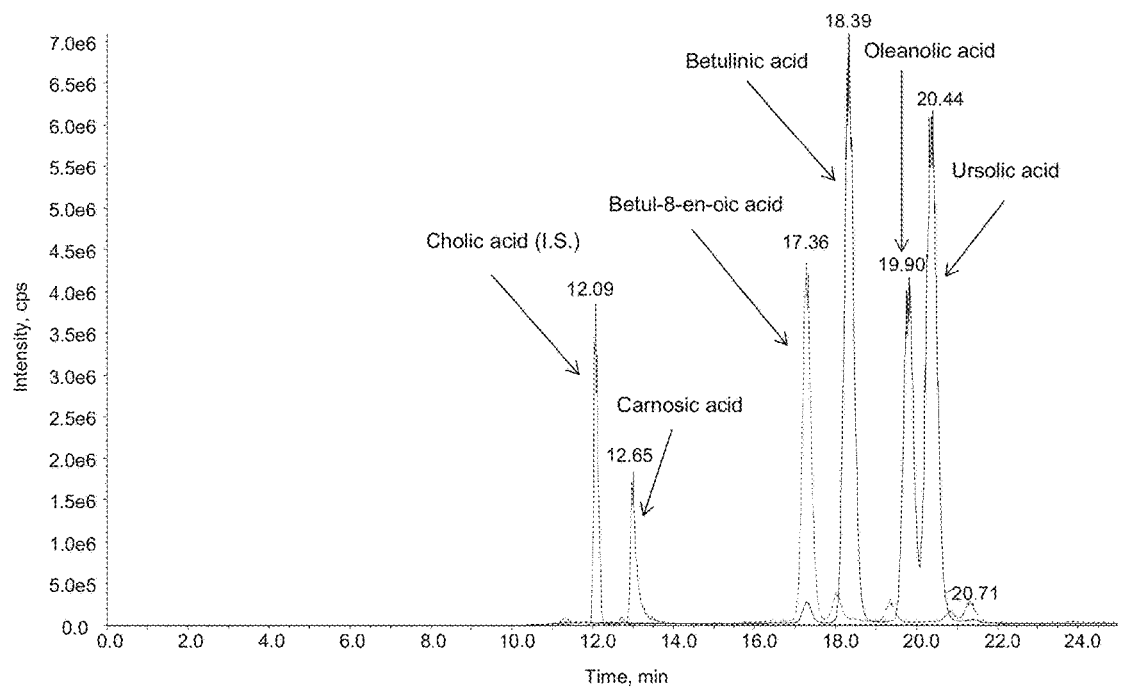
FIG. 10 illustrates the ion chromatogram for the TPM of a cigarette with Camel Blue blend and 5% rosemary obtained using LC-MS/MS, according to some embodiments.

FIG. 10 and Table 7 demonstrate that the transfer of pentacyclic triterpenoid acids, rosmarinic acid, and carnosic acid to the smoke of the sample cigarettes. Carnosic and rosmarinic acid were poorly transferred to the cigarette smoke indicated by the levels detected in the TPM of the sample cigarettes. In contrast, the four pentacyclic triterpenoid acids transferred well to the smoke with quantities of about 14.9 µm/cig of betul-18-en-oic acid, 26.6 µm/cig of betulinic acid, 25.9 µm/cig of oleanolic acid, and 43.3 µg/cig of ursolic acid detected in the TPM of the sample cigarettes. This transfer of betul-18-en-oic acid, betulinic acid, oleanolic acid, and ursolic acid indicates that these acids will be transferred and ingested by a smoker upon drawing on a smoking product that includes the heated rosemary and tobacco.

TABLE 7

Levels of Acids in the TPM (μg/cig)

| Rep. No. | Betul-en-ic | Betu-linic | Carnosic | Olea-nolic | Rosmarinic | Ur-solic |
|---|---|---|---|---|---|---|
| 1 | 13.55 | 25.08 | 3.22 | 23.93 | 0.41 | 39.57 |
| 2 | 15.76 | 27.10 | 3.47 | 26.91 | 0.36 | 45.38 |
| 3 | 15.28 | 27.62 | 3.62 | 26.95 | 0.36 | 44.79 |
| Average | 14.86 | 26.60 | 3.44 | 25.93 | 0.38 | 43.25 |
| RSD % | 7.82 | 5.06 | 5.92 | 6.68 | 7.16 | 7.40 |

While certain embodiments have been illustrated and described, it should be understood that changes and modifications can be made therein in accordance with ordinary skill in the art without departing from the technology in its broader aspects.

The embodiments, illustratively described herein may suitably be practiced in the absence of any element or elements, limitation or limitations, not specifically disclosed herein. Thus, for example, the terms "comprising," "including," "containing," shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof.

What is claimed is:

1. A method of preparing a smoking product, the method comprising:
    blending tobacco and heat-treated rosemary, wherein the heat-treated rosemary has been previously air heated at a temperature of about 100° C. to about 200° C. for about 0.5 to about 8 hours to reduce or remove flavorant components compared to an untreated rosemary.

2. The method of claim 1, wherein the heat-treated rosemary has been air heated at a temperature of about 125° C. to about 175° C. for about 0.5 to about 6hours.

3. The method of claim 2, wherein the heat-treated rosemary has been air heated at a temperature of about 140° C. to about 160° C. for about 1 to about 4 hours.

4. The method of claim 1, wherein the heat-treated rosemary contains less than about 0.3 wt % of 1,8-cineole.

5. The method of claim 1, wherein the heat-treated rosemary contains less than about 0.1 wt % of camphor.

6. The method of claim 1, wherein the heat-treated rosemary contains less than about 0.1 wt % of borneol.

7. The method of claim 1, wherein the heat-treated rosemary contains about 50 wt % to about 99 wt % less 1,8-cineole, camphor, and borneol compared to the untreated rosemary.

8. The method of claim 1, wherein the heat-treated rosemary comprises one or more pentacyclic triterpenoid acids.

9. The method of claim 8, wherein the pentacyclic triterpenoid acids are selected from betulinic acid, oleanolic acid, ursolic acid, betul-18-enoic acid, and combinations thereof.

10. The method of claim 8, wherein the heat-treated rosemary contains no less than about 75 wt % of the pentacyclic triterpenoid acids present in the untreated rosemary.

11. The method of claim 8, wherein the heat-treated rosemary contains about 75 wt % to about 90 wt % of the pentacyclic triterpenoid acids present in the untreated rosemary.

12. The method of claim 1, wherein the smoking tobacco product comprises about 1 wt % to about 10 wt % of the heat-treated rosemary.

13. The method of claim 1, wherein the smoking tobacco product comprises about 1 wt % to about 5 wt % of the heat-treated rosemary.

* * * * *